(12) United States Patent
Gargiulo et al.

(10) Patent No.: US 12,232,853 B2
(45) Date of Patent: Feb. 25, 2025

(54) PHYSIOLOGICAL PARAMETER SENSING SYSTEMS AND METHODS

(71) Applicants: 3 AIM IP PTY LTD., North Sydney (AU); 3 AIM IP PTY LTD., North Sydney (AU)

(72) Inventors: Gaetano Gargiulo, Kogarah (AU); Emilio Andreozzi, Naples (IT); Daniele Esposito, San Martiano Valle Caudina (IT); Paolo Bifulco, Naples (IT)

(73) Assignee: 3 AIM IP PTY LTD., North Sydney (AU)

( * ) Notice: Subject to any disclaimer, the term of this patent is extended or adjusted under 35 U.S.C. 154(b) by 0 days.

(21) Appl. No.: 17/768,162

(22) PCT Filed: Oct. 15, 2020

(86) PCT No.: PCT/AU2020/051107
§ 371 (c)(1),
(2) Date: Apr. 11, 2022

(87) PCT Pub. No.: WO2021/072493
PCT Pub. Date: Apr. 22, 2021

(65) Prior Publication Data
US 2024/0090775 A1 Mar. 21, 2024

(30) Foreign Application Priority Data
Oct. 18, 2019 (AU) .............................. 2019903937

(51) Int. Cl.
*A61B 5/02* (2006.01)
*A61B 5/00* (2006.01)
(Continued)

(52) U.S. Cl.
CPC .......... *A61B 5/0205* (2013.01); *A61B 5/6831* (2013.01); *A61B 5/6833* (2013.01);
(Continued)

(58) Field of Classification Search
CPC .......... A61B 2090/065; A61B 2562/06; A61B 5/0205; A61B 5/021; A61B 5/02438; A61B 5/02444; A61B 5/1102; A61B 5/113; A61B 5/6831; A61B 5/6833; A61B 2560/0223; A61B 2562/0247; A61B 2562/16; A61B 2562/225; A61B 5/02028; A61B 5/029;
(Continued)

(56) References Cited

U.S. PATENT DOCUMENTS

2017/0156706 A1* 6/2017 Joseph ............... A61B 5/02125

* cited by examiner

*Primary Examiner* — Amanda K Hulbert
(74) *Attorney, Agent, or Firm* — Nolte Lackenbach Siegel; Myron Greenspan

(57) ABSTRACT

An apparatus 100 for sensing a physiological parameter of a subject comprises a force sensor 102 configured to generate a first signal representing force displacement of an organ of the subject and a displacement sensor 104 associated with the force sensor 102. The displacement sensor 104 is configured to generate a second signal representing displacement velocity of the organ of the subject. A coupler 106 is arranged on one of the force sensor 102 and the displacement sensor 104, the coupler 106 being configured to mechanically couple the force sensor 102 and the displacement sensor 104 with the organ.

26 Claims, 29 Drawing Sheets

(51) Int. Cl.
    *A61B 5/0205*     (2006.01)
    *A61B 5/021*     (2006.01)
    *A61B 5/029*     (2006.01)
    *A61B 5/08*     (2006.01)
    *A61B 90/00*     (2016.01)

(52) U.S. Cl.
    CPC ............ *A61B 5/02028* (2013.01); *A61B 5/021* (2013.01); *A61B 5/029* (2013.01); *A61B 5/08* (2013.01); *A61B 5/4356* (2013.01); *A61B 5/4362* (2013.01); *A61B 2090/065* (2016.02); *A61B 2560/0223* (2013.01); *A61B 2562/0247* (2013.01); *A61B 2562/06* (2013.01); *A61B 2562/16* (2013.01); *A61B 2562/225* (2013.01)

(58) Field of Classification Search
    CPC ....... A61B 5/08; A61B 5/4356; A61B 5/4362; G01L 1/2237; G01L 1/2268; G01P 3/50; H03F 1/083; H03F 1/26; H03F 1/34; H03F 2200/261; H03F 2203/45138; H03F 2203/45526; H03F 2203/45528; H03F 3/45475; H03F 3/70; H03M 1/124; H03M 3/494; H10N 30/302
    See application file for complete search history.

PHYSIOLOGICAL PARAMETER SENSING SYSTEMS AND METHODS

CROSS-REFERENCE TO RELATED APPLICATIONS

The present application claims priority from Australian Provisional Patent Application No 2019903937 filed on 18 Oct. 2019, the contents of which are incorporated herein by reference in their entirety.

TECHNICAL FIELD

This disclosure relates, generally, to sensing of signals and, more particularly, to sensor assemblies for sensing signals relating to at least one physiological parameter of a subject.

BACKGROUND

While a variety of sensors and systems exist to measure signals when placed about a volume, in particular, to measure and monitor physiological parameters of a living subject, providing a useful output signal representative of the parameter being measured continuously and reliably remains a challenge. In addition, to do so while a living subject can comfortably accommodate the sensor/system measuring the parameter is also challenging, particularly where the subject needs to wear the sensor/system for an extended period of time.

In living subjects, the use force-sensitive resistors (FSRs) to sense muscle contraction intensity has been reported.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to a first aspect of the disclosure, there is provided an apparatus for sensing a physiological parameter of a subject, the apparatus comprising: a force sensor configured to generate a first signal representing force displacement of an organ of the subject; a displacement sensor associated with the force sensor, the displacement sensor configured to generate a second signal representing displacement velocity of the organ of the subject; and a coupler arranged on one of the force sensor and the displacement sensor, the coupler configured to mechanically couple the force sensor and the displacement sensor with the organ.

The force sensor may comprise a first force-sensing resistor (FSR). The displacement sensor may comprise a piezoelectric sensor. The organ may skin.

The coupler may have a maximum planar surface area which is less than a maximum planar surface area of the force sensor. Further, the maximum planar surface area of the coupler may approximate a maximum planar surface area of the displacement sensor.

The force sensor may be mounted to the displacement sensor.

The force sensor may comprise an operatively front surface coupled to an operatively rear surface of the coupler and an operatively rear surface coupled to an operatively front surface of the displacement sensor.

In another embodiment, the force sensor and the displacement sensor may each have an operatively front surface coupled to an operatively rear surface of the coupler. The force sensor and the displacement sensor may be arranged concentrically on the operatively rear surface of the coupler.

The coupler may comprise a front surface configured to contact the organ. The front surface may be dome shaped or mushroom shaped or cone shaped or pyramid shaped. Instead, the coupler may be cylindrical or cuboid. The coupler may comprise at least one of a rigid plastics material, such as acrylic resin, and a conductive material.

The apparatus may further comprise a second force sensor configured to measure a force applied to an operatively rear surface of the apparatus. The second force sensor may be a force-sensing resistor (FSR). The second force sensor may be coupled to an operatively rear surface of the displacement sensor.

The apparatus may further comprise a fixing device configured to secure the apparatus to the organ of the subject. The fixing device may comprise at least one of: a) a strap; b) a belt; c) an adhesive patch.

The apparatus may further comprise at least one processor configured to determine the physiological parameter based on the first signal and the second signal. The at least one processor may be configured to: calibrate the second signal received from the displacement sensor based on the first signal.

The physiological parameter may comprise at least one of a cardiac parameter, such as a cardiac impulse, a blood pressure, such as central blood pressure or peripheral blood pressure, a uterine contraction, foetal activity, respiration, body sounds such as heart sounds, an opening time of a heart valve of the subject, a closure time of a heart valve of the subject, a contractility level of a heart of the subject, a stroke volume of a heart of the subject, a cardiac output, and a blood pulse transit time.

According to another aspect of the disclosure, there is provided a method of measuring a physiological parameter of a subject, the method comprising: receiving a first signal from a first force sensor mechanically coupled to skin at a first location on the subject; receiving a second signal from a second force sensor mechanically coupled to skin at a second location on the subject, the second location being separated from the first location; and determining the physiological parameter based on a comparison of the first and second signals.

The comparison may comprise a difference between the first signal and the second signal.

One or more of the first force sensor and the second force sensor may be a force-sensing resistor (FSR).

The physiological parameter may comprise at least one of a cardiac parameter, such as a cardiac impulse, a blood pressure, such as central blood pressure or peripheral blood pressure, a uterine contraction, foetal activity, respiration, body sounds such as heart sounds, an opening time of a heart valve of the subject, a closure time of a heart valve of the subject, a contractility level of a heart of the subject, a stroke volume of a heart of the subject, a cardiac output, and a blood pulse transit time.

The first location may be on an upper thorax of the subject, such as at or near the xiphoid process. The second location may be on a lower thorax of the subject. The physiological parameter to be measured may be central blood pressure.

In another embodiment, the first location may be on a thorax of the subject. The second location may be proximate to one of a femoral artery and a subclavian artery, or other peripheral artery, of the subject. The physiological parameter to be measured in such cases may be peripheral blood pressure.

The method may further comprise receiving a third signal from a third force sensor mechanically coupled to the skin at a third location separated from the first location and the second location and determining the physiological parameter based on a comparison of the first signal, the second signal and the third signal. The third force sensor may be an FSR.

The method may further comprise mechanically coupling one or more of the first sensor and the second sensor to the skin of the subject.

According to another aspect of the disclosure, there is provided a system for measuring a physiological parameter of a subject, the system comprising: a first force sensor configured to generate a first signal representing force displacement at a first location on the skin of the subject; a second force sensor configured to generate a second signal representing force displacement at a second location on the skin of the subject; and at least one processor configured to determine the physiological parameter of the subject based on a comparison between the first signal and the second signal.

The comparison may comprise a difference between the first signal and the second signal.

At least one of the first force sensor and the second force sensor may be a force-sensing resistor (FSR).

The physiological parameter may comprise a cardiac parameter, such as a cardiac impulse, or a blood pressure, such as central blood pressure or peripheral blood pressure, a uterine contraction, foetal activity, respiration, body sounds such as heart sounds, an opening time of a heart valve of the subject, a closure time of a heart valve of the subject, a contractility level of a heart of the subject, a stroke volume of a heart of the subject, a cardiac output, and a blood pulse transit time.

The first location may be on an upper thorax of the subject, such as at or near the xiphoid process. The second location may be on a lower thorax of the subject. The physiological parameter to be measured may be central blood pressure.

In another embodiment, the first location may be on a thorax of the subject. The second location may be proximate to one of a femoral artery and a subclavian artery, or other peripheral artery, of the subject. The physiological parameter to be measured in such cases may be peripheral blood pressure.

The system may further comprise third force sensor configured to generate a first signal representing force displacement at a third location on the skin of the subject separated from the first location and the second location. The physiological parameter may then be determined based on a comparison of the first signal, the second signal and the third signal. The third force sensor may be an FSR.

One or more of the first force sensor and the second force sensor may be the first force sensor of an apparatus as described above.

According to another aspect of the disclosure, there is provided an apparatus for sensing at least one parameter of a subject, the apparatus comprising: a flexible sensor member having an impedance which changes with flexure; and a flexible carrier surrounding the flexible sensor member and configured to maintain a contact surface of the flexible sensor member proximate a surface of the subject such that a change of shape, such as radius, of the surface of the subject causes the flexible sensor to flex.

The flexible sensor member may comprise force-sensing resistor (FSR).

The carrier may be at least one of a fabric carrier and an elastomeric carrier. The carrier may comprise a strap or an adhesive patch. The carrier may comprise a garment worn by the subject. The garment may comprise a shirt, or a vest, or a jacket, or a coat.

The surface of the subject may be skin, such as the skin at a thorax of the subject. The flexible carrier may be configured to maintain the contact surface proximate to the skin such that expansion and contraction of the skin (e.g. expansion and contraction of the thorax due to respiration) causes the flexible sensor to flex.

The apparatus may further comprise at least one processor configured to generate the at least one parameter based on the impedance of the flexible sensor member.

The parameter may comprise a cardiac parameter, such as a cardiac impulse, or a blood pressure, such as central blood pressure or peripheral blood pressure, or uterine contraction, foetal activity, respiration, body sounds such as heart sounds, an opening time of a heart valve of the subject, a closure time of a heart valve of the subject, a contractility level of a heart of the subject, a stroke volume of a heart of the subject, a cardiac output, and/or a blood pulse transit time.

According to another aspect of the disclosure, there is provided a method of sensing at least one parameter of a subject, the method comprising: locating a flexible sensor as described above at a first location proximate an organ of a subject; and determining the at least one parameter based on the impedance of the flexible sensor member.

BRIEF DESCRIPTION OF DRAWINGS

Embodiments of the disclosure are now described by way of example with reference to the accompanying drawings in which:

FIG. 24 is a plot showing raw data relating to respiration derived from the sensor assembly of FIG. 1a:

Figu

Figure 1A:
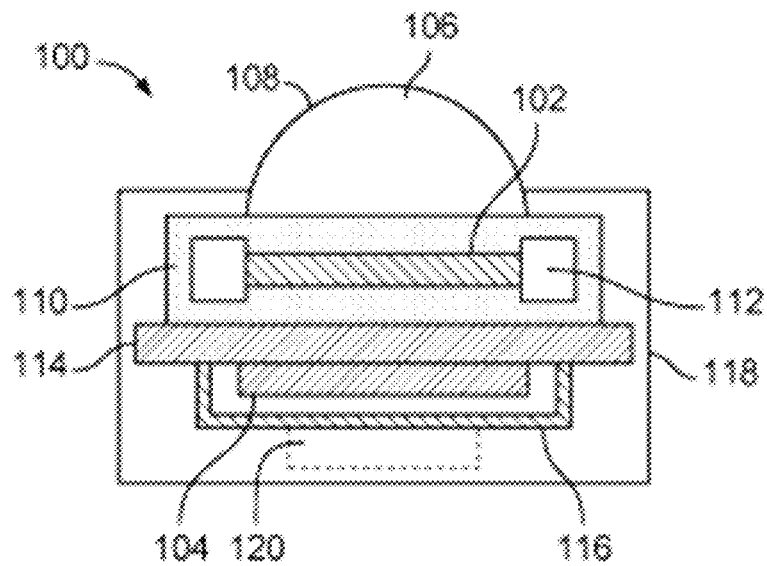
FIG. 1a is a schematic diagram of a first embodiment of a sensor assembly.
Figure 26:
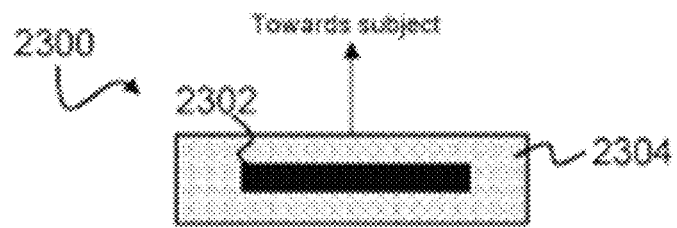
Figure 27:
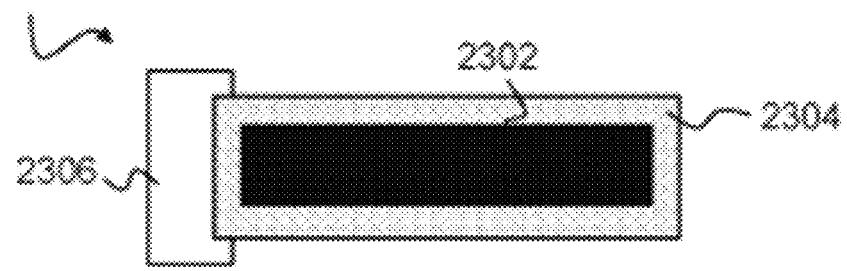
Figure 28:
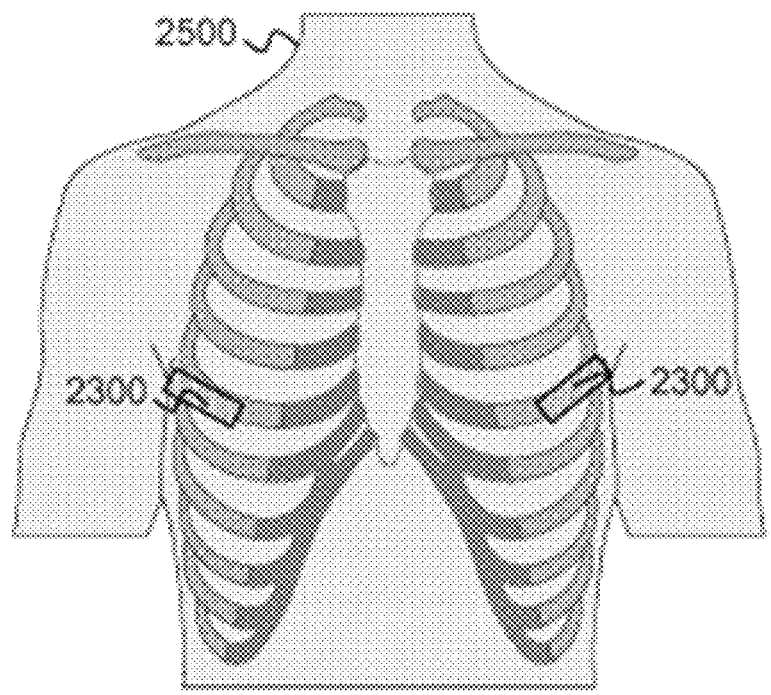
Figure 29:
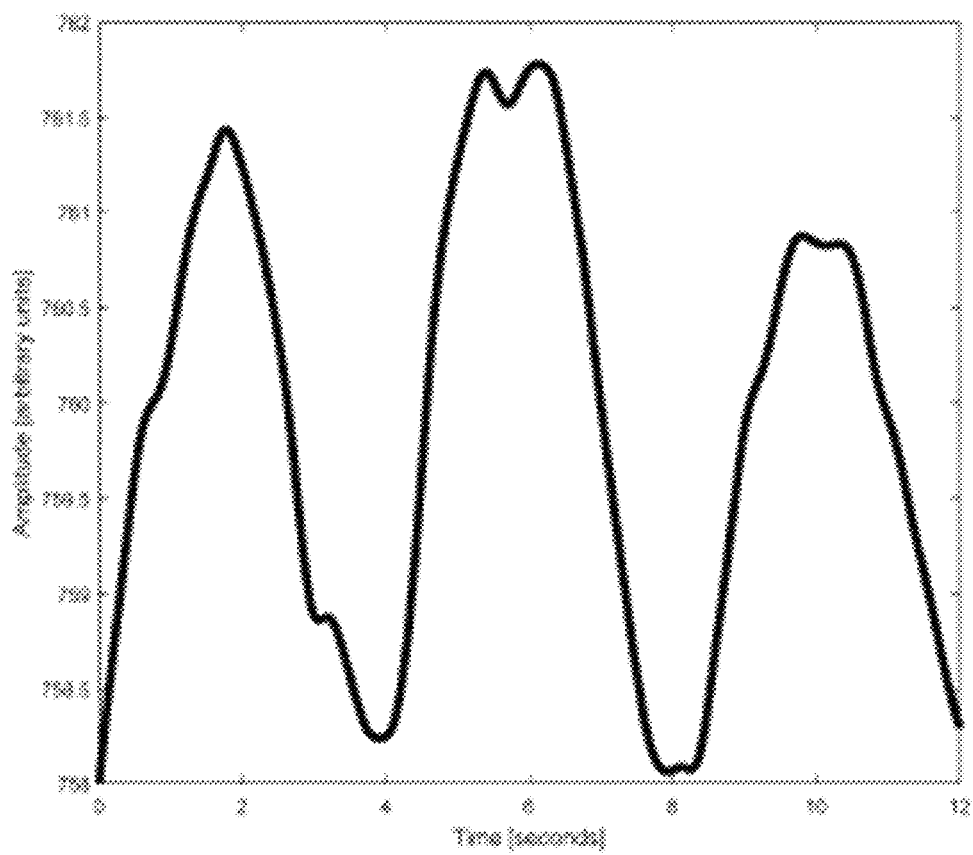
Figures 30, 31:
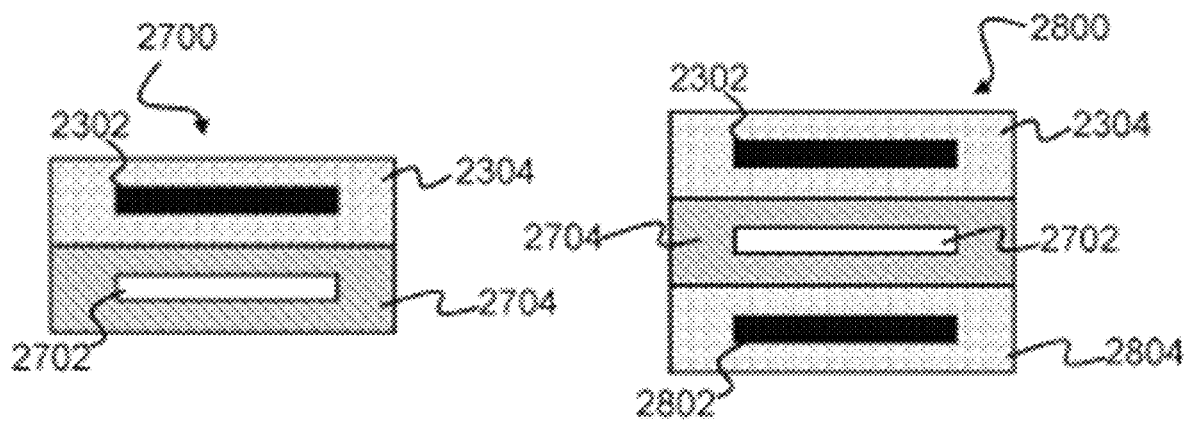
Figure 32:
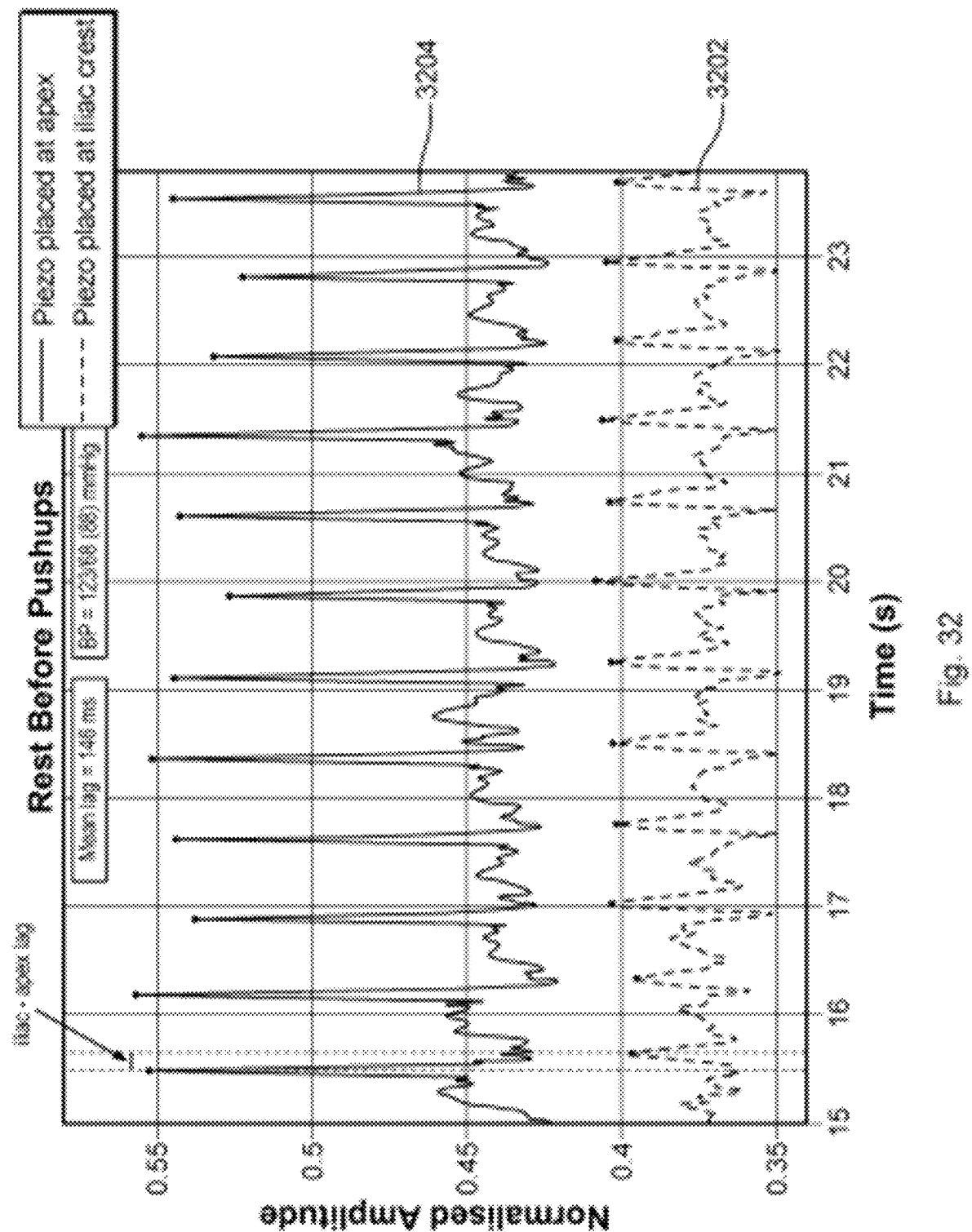
Figure 33:
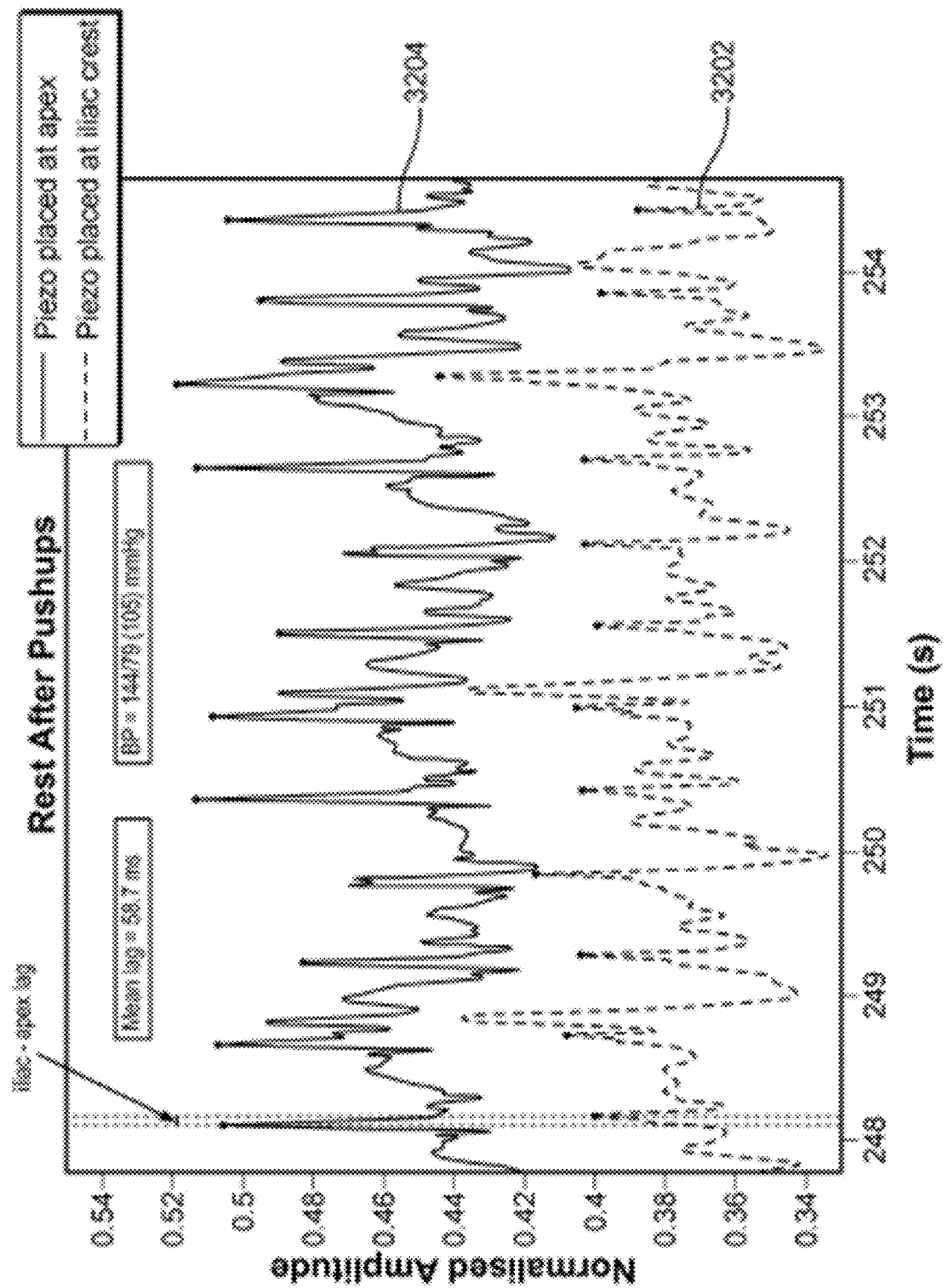
Figure 34:
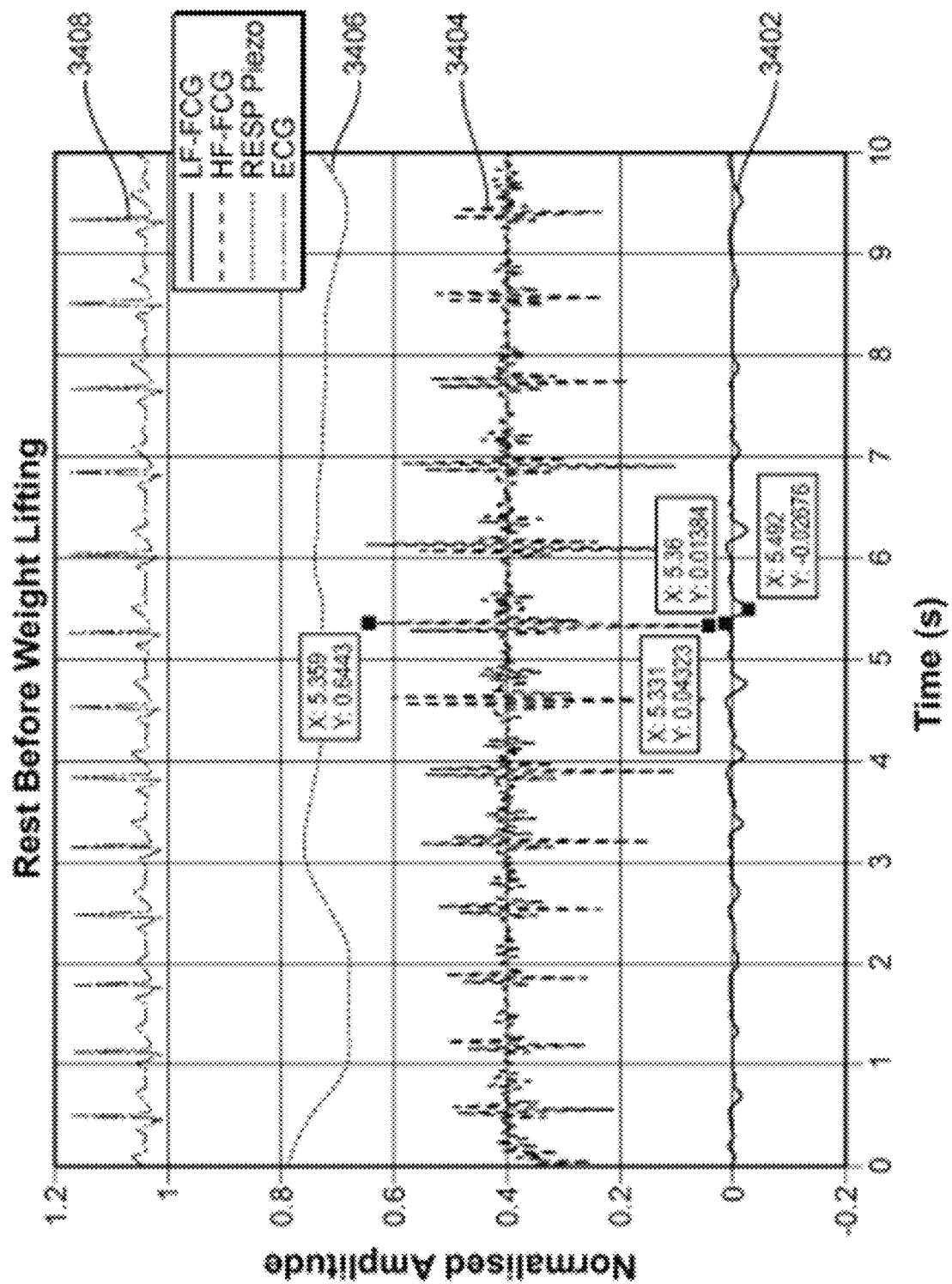
Figure 35:
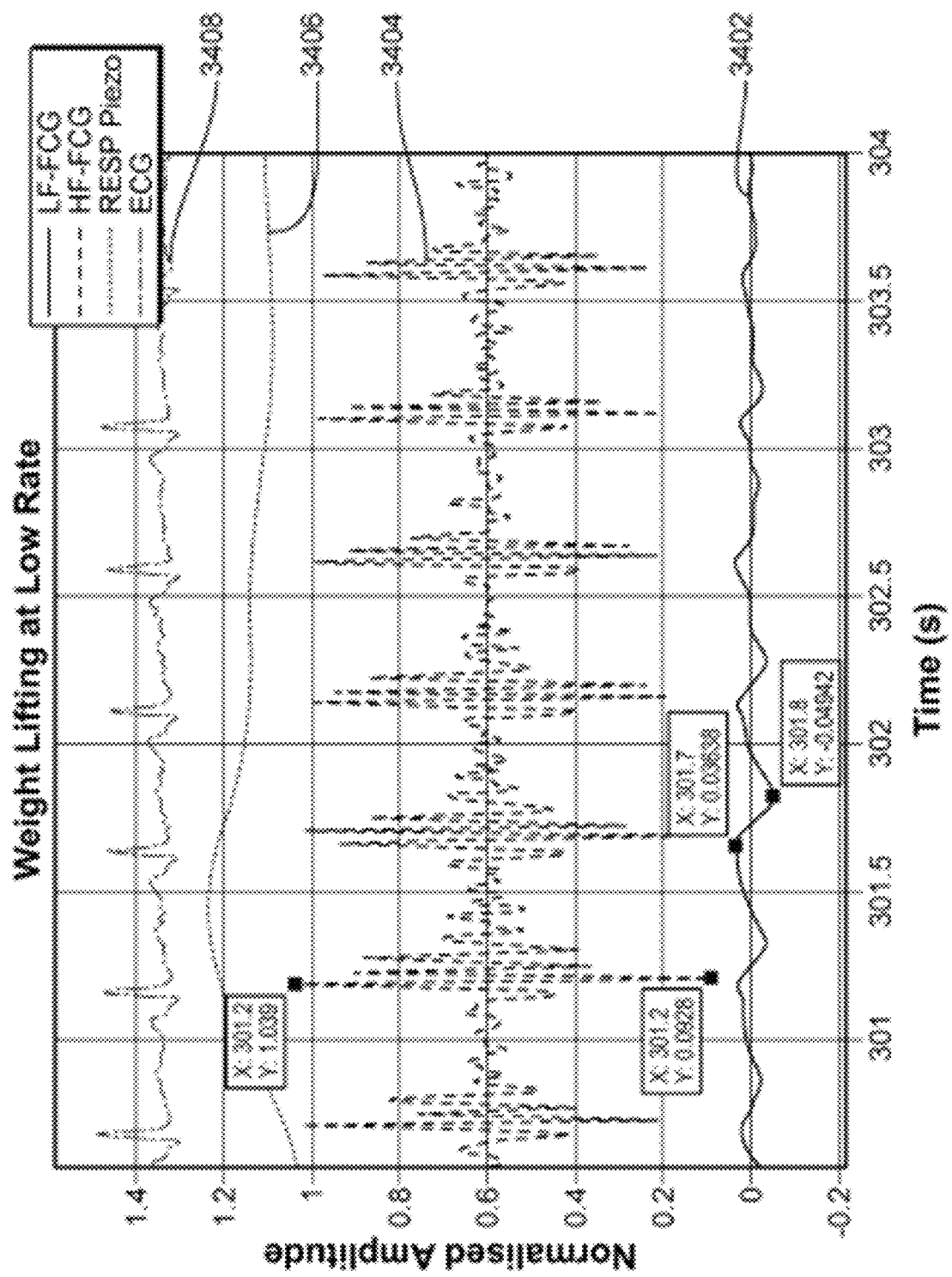
Figure 36:
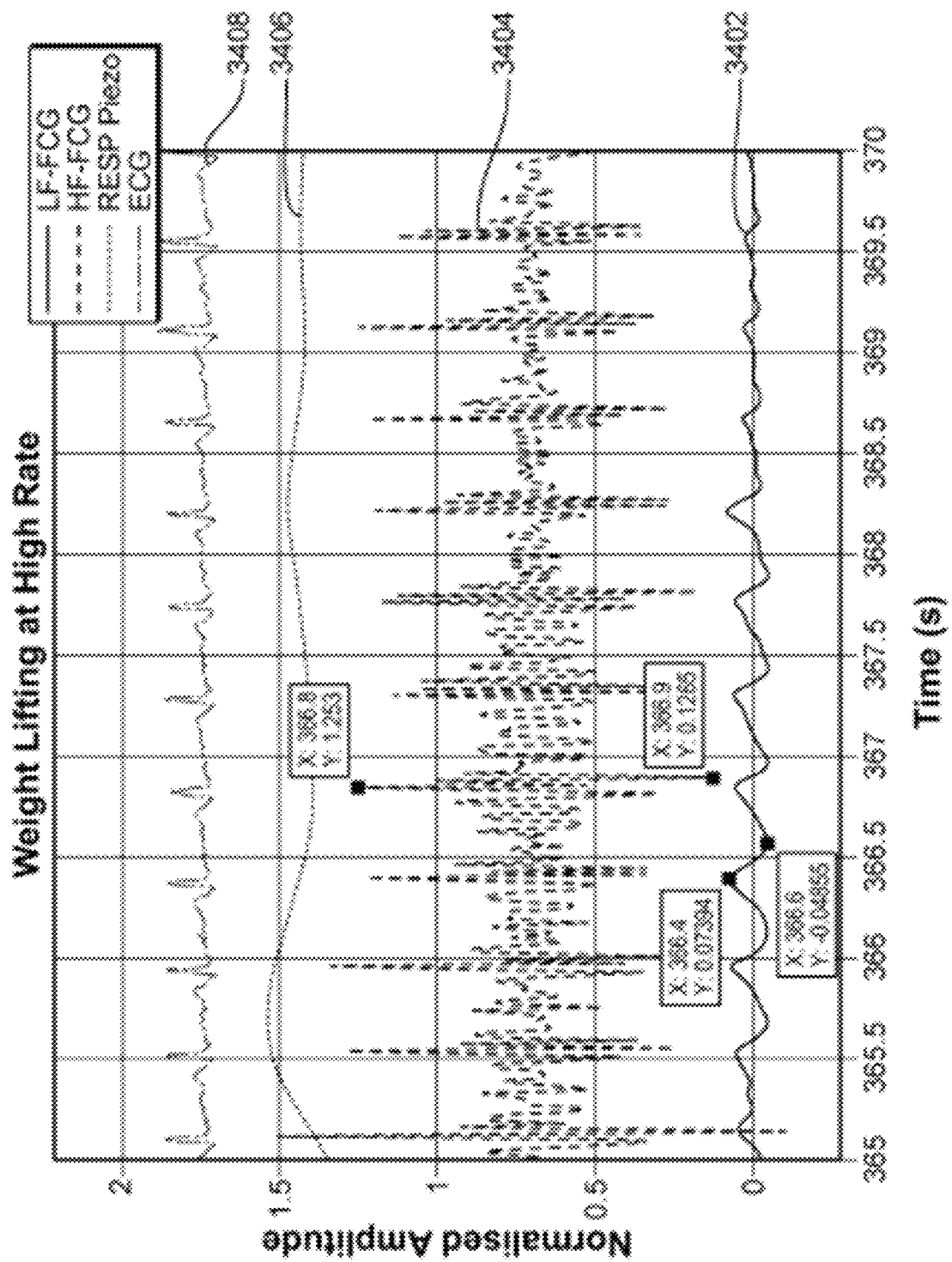

FIG. 26 is a cross-section view of an embodiment of a sensor assembly;

FIG. 27 is a plan view of the embodiment of the sensor assembly shown in FIG. 26;

FIG. 28 shows a pair of the sensor assemblies of FIG. 26 arranged on a thorax of a subject;

FIG. 29 is a breathing signal derived from the sensor assembly of FIG. 26;

FIG. 30 is a cross-section view of a further embodiment of a sensor assembly;

FIG. 31 is a cross-section view of another embodiment of a sensor assembly;

FIG. 32 is a plot of pulse transit time (PTT) as derived from the sensor assembly of FIG. 1a with the subject at rest;

FIG. 33 is a plot of the PTT as derived from the sensor assembly of FIG. 1a after exertion by the subject;

FIG. 34 is a plot of cardiac activity as derived from the sensor assembly of FIG. 1a with the subject at rest;

FIG. 35 is a plot of the cardiac activity as derived from the sensor assembly of FIG. 1a after low rate exertion by the subject; and FIG. 36 is a plot of the cardiac activity as derived from the sensor assembly of FIG. 1a after higher rate exertion by the subject.

DESCRIPTION OF EMBODIMENTS

Embodiments of the present disclosure relate to sensing systems and methods for monitoring physiological mechanics from local measurements of force and their propagation speed exerted by displacement of skin surfaces by organs, muscles, blood flow, and fluids shifts, i.e. digestion, deglutition, respiration, etc.

Some embodiments use force sensors, such as force sensitive resistors (FSRs), mechanically coupled with a subject's skin on the thorax or upper abdomen, to measure recoil forces generated by the cardiac contraction and blood pumping action, so called "Forcecardiography (FCG)". Embodiments can thus enable continuous and non-invasive monitoring of mechanical events of each cardiac cycle of a subject. Particularly by using multiple force sensors mechanically coupled with a subject's skin, information on physiological parameters can be obtained, such as identification and duration of each phase of a cardiac cycle, heart valves opening and closure timing, heart contractility level, stroke volume, cardiac output, pulse transit time, and central arterial pressure. In turn, information can be obtained about heart diseases and/or malfunctions, such as but not limited to heart failures, mechanical dyssynchrony (e.g. as results of bundle branch blocks), valvular pathologies (e.g. aortic and mitral regurgitation, stenosis), etc.

When provided in proximity of peripheral pulse points or major vessels (i.e. neck pulse, radial pulse, etc.), force sensors can be used to measure force and their propagation speed of blood movements and flow. Such flow may include venous return as well as changes in hydrostatic pressure due to respiration. As such, embodiments make it possible to infer respiratory rate from force measurements of the peripheral limbs.

Some embodiments use one or more force sensors (such as FSRs) in combination with a displacement sensor (such as a piezoelectric sensor), both mechanically coupled with the subject's skin, to simultaneously measure force displacement of the subject's skin and speed or velocity of such displacement. The compression force (DC baseline of the force sensor signal) and the dynamic force (AC component of force sensor signal) exerted on the force sensor can be used to calibrate the displacement velocity signal generated by the displacement sensor, allowing accurate and continuous direct measurement of speed or velocity of displacement of the skin as well as force displacement itself. As such, accurate and continuous measurement blood impulse and therefore cardiac impulse can be obtained from movement of skin alone.

While the sensor assemblies described herein have been developed specifically for measuring physiological parameters, such as, for example, cardiac activity and respiratory activity, of a living subject, those skilled in the art will appreciate that the sensor assemblies which are the subject of the disclosure could be used with other objects where a force is applied by a part underlying the sensor assembly. Thus, sensor assemblies described herein could be used in industrial applications such as soft robotics or other inanimate objects where such force is applied.

FIG. 1a is a cross-sectional diagram of a first embodiment of a sensor assembly 100 for sensing at least one physiological parameter of a subject. The sensor assembly 100 comprises a force sensor 102, a displacement sensor 104 and a mechanical coupler 106. The force sensor 102 and the displacement sensor 104 are arranged on the coupler 106 such that any force applied to a front surface 108 of the coupler is transferred to both the force sensor 102 and the displacement sensor 104.

The coupler 106 comprises a rigid material such as rigid plastic or rubber. In some embodiments, the coupler 106 may comprise an acrylic resin. In other embodiments, the coupler 106 may be partially or wholly conductive. For example, the coupler 106 may partially or wholly comprise a conductive material, such as silver or silver chloride. The front surface 108 of the coupler 106 configured to face and preferable be placed in contact with a surface of the subject may be dome shaped so as to depress into a compliant surface of the subject, such as skin. Providing a dome shaped front surface 108 assists in improving the coupling of mechanical displacement from the subject to the force sensor 102 and the displacement sensor 104. Other shapes for the front surfaces 108 providing a similar effect include cone shapes, mushroom shapes, etc.

The coupler 106 has a generally circular cross-section when viewed in a plane parallel to the subject facing plane of the sensor assembly 100. In addition to coupling movement (force and displacement), the coupler 106 may be configured as a biopotential electrode and may be electrically coupled to processing circuitry (not shown) for measuring biopotential (e.g. electrocardiography (ECG), electromyography (EMG), electroencephalography (EEG), etc.

The force sensor 102 is mounted to a rear surface of the coupler 106 via a force sensor carrier 110 which comprises a flexible medium. The force sensor 102 is mounted to the carrier 110 by glue, lamination, or otherwise. Electrical connections to the force sensor 102 are made using two or more electrodes 112 which also act as anchoring points to anchor the force sensor 102 to the sensor carrier 110. The force sensor 102 is a force sensitive resistor (FSR) or a load cell. As will be described in more detail below, a characteristic of the force sensor 102 changes in response to a force signal being applied to the force sensor, the change representing a force displacement of an organ in contact with the front surface 108 of the coupler 106. Such a characteristic is, for example, the impedance of the force sensor 102 or an output current or voltage. Where the force sensor 102 is an FSR, changes in resistance of the force sensor 102 represent force displacement from which an output voltage can be generated, as will be described below in more detail.

In an embodiment, a front surface of the force sensor 102 facing toward the subject in use has a surface area of between about 5 mm and 10 mm, for example, 7 mm, 8 mm or 9 mm.

The force sensor 102 and the displacement sensor 104 are mounted together via an optional a rigid interface layer 114. The rigid interface layer 114 is provided on a rear surface of the force sensor 102. The rigid interface layer 114 may comprise brass, rigid plastic, or similar rigid material. In some embodiments, the rigid interface layer 114 may be a double sided PCB, the force sensor 102 mounted on a first surface of the PCB (i.e. the surface facing the subject in use) and the displacement sensor 104 being mounted on an opposed, second surface of the PCB.

In any case, the displacement sensor 104 is mechanically coupled to the rear surface of the force sensor 102 as shown in FIG. 1a. Thus displacement of the coupler 106 due to movement of the organ in contact with the coupler 106 causes the displacement sensor 104 to move. The displacement sensor 104 generates a velocity signal representing a speed or velocity of displacement of the sensor 104. When mechanically coupled to an organ such as the skin of a subject, this velocity signal is proportional to a displacement velocity of the organ.

In an embodiment, a front, subject-facing surface of the displacement sensor 104 has a surface area of between about 5 mm and 10 mm, for example, 7 mm, 8 mm or 9 mm.

Advantageously, the surface area of the force and displacements sensors 102, 104 are substantially matched to ensure uniform transfer of displacement from the force sensor 102 to the displacement sensor 104. The force and displacement sensors 102, 104 are therefore also preferably axially aligned along a central, operatively vertical axis of the assembly 100 for similar reasons.

An optional protective cover 116 may be provided around a rear surface of the displacement sensor 104. The protective cover 116 may be separated from the rear surface by a fluid gap filled with air or other gas, or a vacuum. In doing so, the protective cover 116 protects the displacement sensor 104 from impacts on the operatively rear, non-subject facing side of the assembly 100.

In addition to the force sensor 102 and the displacement sensor 104, the sensor assembly 100 may optionally comprise an accelerometer 120. The accelerometer 120 is configured to measure acceleration in one or more axes. For example, the accelerometer 120 may be configured to measure acceleration at least in an axis perpendicular to the surface of the subject to which the sensor assembly 100 is affixed in use. Preferably, additionally, the accelerometer 120 measures acceleration in one or more planes parallel to the surface of a subject to which the sensor assembly 100 is affixed in use, so as to measure movement of the sensor assembly in such a plane(s) or axes. The accelerometer 120 may be positioned at any location on the sensor assembly 100 provided mechanical coupling is provided (direct or indirect) to the coupler 106. For example, the accelerometer 120 may be coupled to the rear of the protective cover 116.

A housing 118 encapsulates the sensor assembly 100 to protect elements of the assembly 100 from detritus such as dust, grit, water, and/or any other matter that might affect operation of the assembly 100 and to inhibit the ingress of foreign bodies into the assembly 100. The operative, front surface 108 of the coupler 106 extends through an aperture of the housing 118. Instead, the housing 118 could include at least a flexible portion (not shown) which extends over and conforms to the front surface 108 of the coupler 106 thereby fully encapsulating the force sensor 102, the displacement sensor 104 and the coupler 106.

During operation, the front surface 108 of the coupler 106 of the sensor assembly 100 is placed in contact with a surface of a subject, such as the skin of the subject, the sensor assembly 100 fixed relative to the subject by one or more fixing devices, such as a belt, an adhesive patch, adhesive tape or the like (not shown). Such tape may be made from the material from which sports tape, also known as kinesiology tape, is made. With the force and displacement sensors 102, 104 mechanically coupled to the coupler 106 and the coupler 106 mechanically coupled to the surface of the subject, the sensor assembly 100 is configured to generate simultaneous force displacement and displacement velocity signals. These signals are, in turn, used to enable continuous and non-invasive monitoring of mechanical physiological events as will be described in more detail below.

Figure 1B:
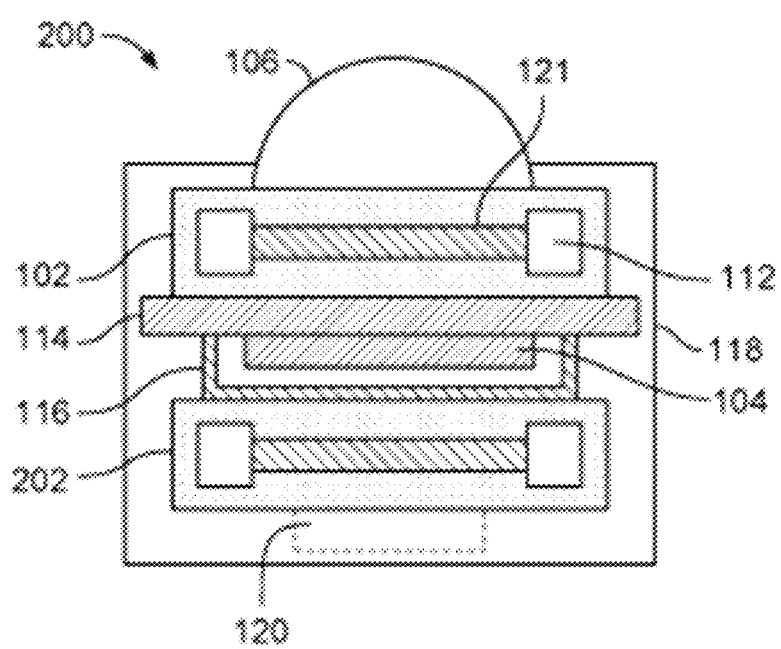
FIG. 1b is a schematic diagram of a second embodiment of a sensor assembly.

FIG. 1b is a cross-sectional diagram of another embodiment of a sensor assembly 200 which is a variation of the sensor assembly 100 shown in FIG. 1a. With reference to FIG. 1a, in FIG. 1b like reference numerals refer to like parts unless otherwise specified.

In addition to the elements of the sensor assembly 100, the sensor assembly 200 of FIG. 1b further comprises a second force sensor 202 similar to the force sensor 102 and having similar features. The second force sensor 202 is mounted operatively rearwardly of the displacement sensor 104, for example to an operatively, outer surface of the protective cover 116. Similar to the force sensor 102, the second force sensor 202 is configured to generate (actively or passively) a signal representative of force applied at the second sensor 202. Thus, the second force sensor 202 is used to measure forces applied to the operatively rear part of the assembly 200, for example, due to one or more fixing devices used to apply the sensor assembly 200 to a surface of a subject.

This measured external force signal is able to be used to compensate for carrier pressure force (i.e. the force applied by fixing devices to the rear of the sensor assembly 200) and surface resilience of the subject (i.e. how resilient the surface of the subject being sensed is). For example, knowing the pressure applied from an external carrier or the operator of the assembly 200 will allow for artefact rejection. For example, a sudden knock or shearing of the sensor i.e. during movements may alter the application of pressure of the force sensor 102 which in turn may create artefacts in the signal from the force sensor 102. Additionally, rhythmic movements caused by activities such as running of the subject may impress a baseline wander and associated artefact to the signal from the force sensor 102. Such artefacts can be cancelled (either in real time or in post processing) using signals derived from each of the two force sensors 102, 202 and the displacement sensor 104, as will be described in more detail below.

Figure 1C:
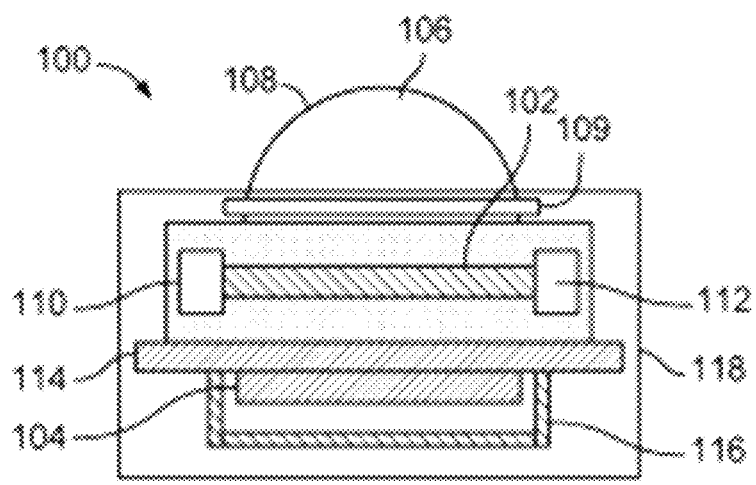
FIG. 1c is a schematic diagram of a third embodiment of a sensor assembly.
Figure 1D:
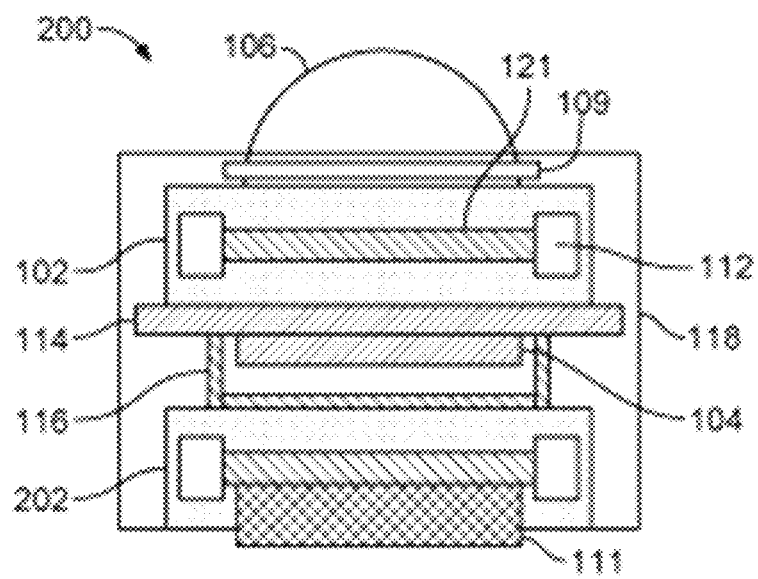
FIG. 1d is a schematic diagram of a fourth embodiment of a sensor assembly.

Referring now to FIGS. 1c and 1d of the drawings, further embodiments of the sensor assemblies 100 and 200 are illustrated. Once again, with reference to the previous drawings, like reference numerals refer to like parts, unless otherwise specified.

In both embodiments, the coupler 106 includes a collar 109 which is received within the housing 118 with the dome-shaped surface 108 of the coupler 106 projecting through an opening (not shown) in the housing 118. The opening has a smaller diameter than that of the collar 109 so that the collar 109 assists in holding the coupler 106 captive relative to the housing 118 and inhibits separation of the coupler 106 from the housing 118.

Further, in both embodiments, the diameter of the coupler 106, at its base, i.e. that part of the coupler 106 in contact with the sensor carrier 110 (referred to as the "base diameter"), is less than that of the force sensor 102. However, it is desirable and preferable that the coupler 106 distributes its force over the entire surface area of the displacement sensor 104. As such, the base diameter of the coupler 106 approximates the diameter of the displacement sensor 104. Typically, the base diameter of the coupler 106 is approximately 70% to 90% and, for example, about 80% of the diameter of the force sensor 102.

In the embodiment shown in FIG. 1d of the drawings, the sensor assembly 200 further includes a rear pressure applicator, or coupler, 111. Typically, this coupler 111 is, in use, overlain by the component by which the sensor assembly 200 is affixed to the organ of the subject, for example, a strap, a belt, tape, or the like (not shown). This component applies a displacement force to the force sensor 202 via the coupler 111 and assists in removing artefacts recorded by the sensor assembly 200 due to extraneous factors such as movement of the sensor assembly 200 relevant to the organ of the subject.

While the coupler 111 has been shown as a plate-like structure, it will be appreciated that the coupler 111 could have any suitable shape including a dome shape similar to that of the coupler 106. Once again, the coupler 111 has a diameter less than that of the force sensor 202, typically approximately 70% to 90% and, for example, about 80% of the diameter of the force sensor 202.

As indicated above, a dome shaped coupler 106 aids in depressing into a compliant surface of the subject, such as skin. Providing a couple 106 with a dome shaped front surface 108 thus improves the coupling of mechanical displacement from the subject to the force sensor 102 and the displacement sensor 104.

The sensor assemblies 100, 200 described above comprise force and displacement sensors in a "sandwich" arrangement stacked relative to one another. However, embodiments of the present disclosure are not limited to such an arrangement. For example, in other embodiments, force and displacement sensors may be arranged in a planar configuration, for example, arranged next to each other or arranged concentrically (one within the other), and may be arranged either on a common substrate or on different, separate substrates. In each embodiment, each force sensor and displacement sensor is preferably mechanically coupled (either directly or indirectly) to a coupler, such as the coupler 106, 111, of FIGS. 1a to 1d so as to ensure mechanical transfer of force from a subject to the each sensor.

FIGS. 2a to 2g show several variations of the coupler 106 of FIGS. 1a to 1d which may be provided in place of the coupler 106 shown in FIGS. 1a and 1b. As before, like reference numerals refer to like parts, unless otherwise specified.

Figure 2A:
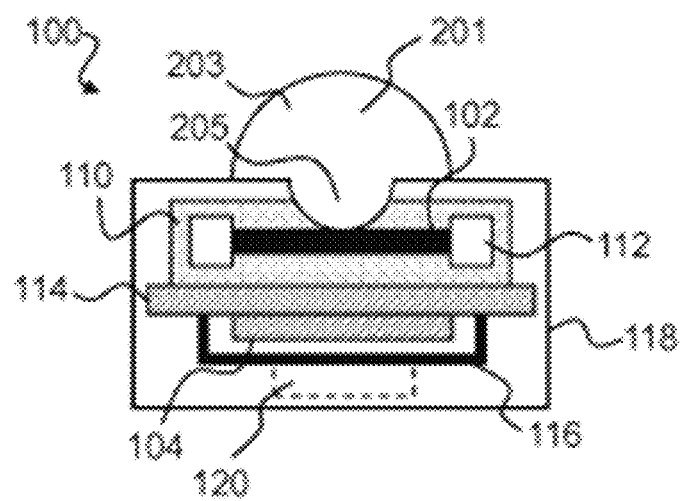
FIGS. 2a to 2g show variations of the coupler of FIGS. 1a and 1b.

FIG. 2a is a cross-sectional view of the sensor assembly 100 having a mushroom shaped coupler 201 comprising a domed front surface 203 and as well as a domed rear surface 205 configured to contact the force sensor 102. Providing a domed rear surface 205 creates a smaller surface area of contact between the coupler 201 and the force sensor 102, thereby increasing the force applied to the sensor per unit area, which in turn increases the sensitivity of the sensor 102 to force applied to the front surface of the coupler 201.

Figure 2B:
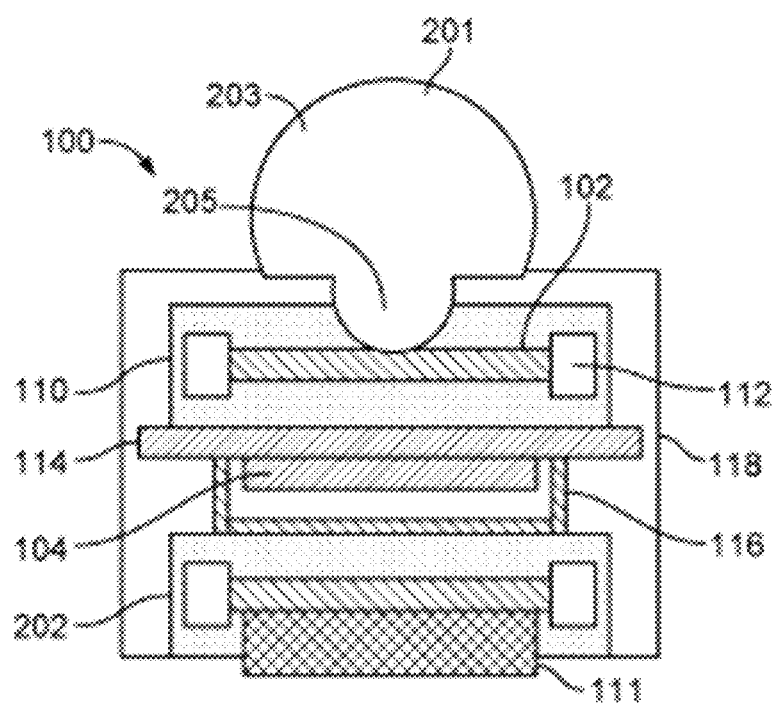

FIG. 2b shows an embodiment of a sensor assembly 100 similar to that of FIG. 2a but including the coupler 111 acting against the force sensor 202 as described above with reference to the sensor assembly 202 of FIG. 1d.

Figure 2C:
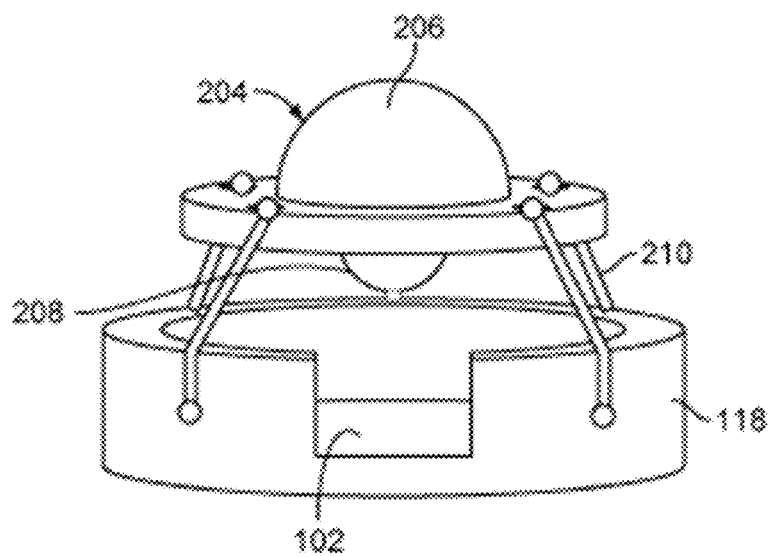
Figure 2D:
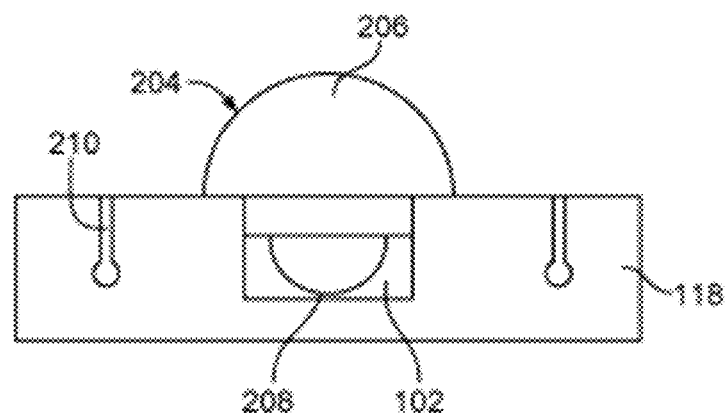

FIGS. 2c and 2d provide, respectively, perspective (expanded) and side views of a coupler 204 comprising a domed front surface 206 as well as a domed rear surface 208 configured for contact with the force sensor 208, similar to the coupler 201 of FIGS. 2a and 2b. Optionally, the coupler 204 is held in place relative to the housing 118 and the force sensor 102 with one or more fasteners 210 such as elastic or elastomeric links. In other embodiments, the coupler 204 may be held in place by rear pressure on the housing 118 and contact with the surface of a subject and a carrier (not shown). As shown in FIG. 2d, providing a domed rear surface 208 creates a small surface area of contact between the coupler 204 and the force sensor 102, thereby increasing the force applied to the sensor per unit area which, in turn, increases the sensitivity of the sensor 102 to force applied to the front surface of the coupler 204. As described above in relation to the coupler 106, it has been found that providing a dome shaped front surface 206 improves the coupling of mechanical displacement from the subject to the force sensor 102 and the displacement sensor 104. Other shapes for the front surface 206 and the rear surface 208 providing a similar effect include cone shapes, mushroom shapes, etc.

Figure 2E:
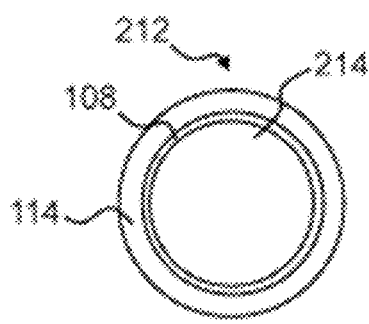
Figure 2F:
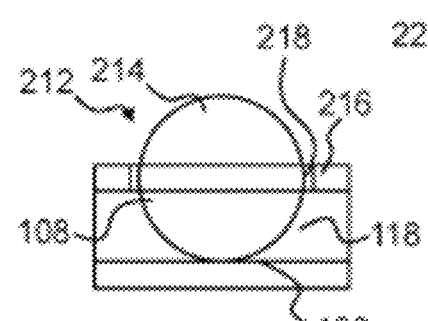

FIGS. 2e and 2f show a further coupler 212 which is a variation of the coupler 204. The coupler 212 comprises a ball or sphere 214 supported within the housing 118 by a lip 216 extending around the circumference of the ball 214. The lip 216 may form part of the housing 118. Optionally, a seal 218 such as a gasket or O-ring, is provided between the ball 214 and the lip 216 to inhibit ingress of dirt and other detrimental matter.

Figure 2G:
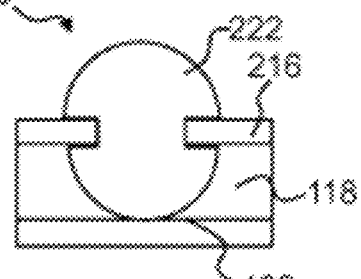

FIG. 2g shows a coupler 220 which is a variation of the coupler 212 in which the ball 214 has been replaced with a double mushroom or waisted coupling member 222. The waisted portion of the coupling member 222 is engaged and held in place in the coupler 220 by the lip 216, which also inhibits separation of the coupling member 222 from the housing 118.

The sensor assemblies 100, 200 described above each comprise a displacement sensor 104. It is noted however, that embodiments of the present disclosure are not limited to using the combination of force and displacement sensors. For example, various novel techniques will be described below, for using multiple force sensors positioned at different locations on a subject for detecting various physiological parameters. Such techniques do not require simultaneous displacement sensing. Such techniques may use the sensor assemblies 100, 200 described above, or alternatively may use sensor assemblies comprising only a force sensor and a coupler. Such sensor assemblies may comprise any conceivable coupling arrangement, for example one of the arrangements shown in any one of FIGS. 1a to 2g. For example, embodiments may use a variation of the sensor assembly 100 shown above but omitting the displacement sensor 104.

FIGS. 3 to 6 show various arrangements of sensor assemblies such as the sensor assembly 100 of FIG. 1a, the sensor assembly 200 of FIG. 1b or a variation thereof, fixed to a living human subject 300.

Figure 3:
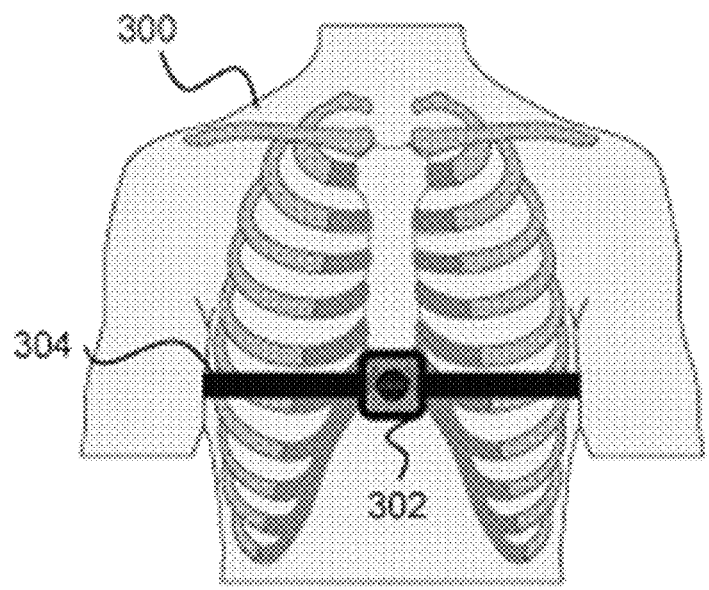
FIGS. 3 to 6 show embodiments of a sensor assembly in various arrangements on a human subject.

In FIG. 3, a single sensor assembly 302 is fixed relative to the xiphoid process using a chest belt 304. The chest belt 304 is configured to apply external pressure from the rear of the sensor assembly 302 and maintain the sensor assembly 302 at or near the xiphoid process.

Figure 4:
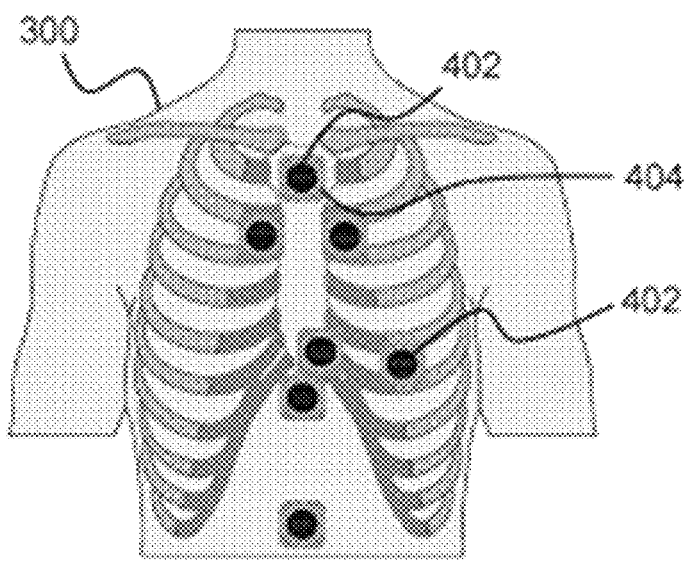

In FIG. 4, multiple sensor assemblies 402 are fixed to the skin of the subject 300 using adhesive patches 404. Like the chest belt 304, each adhesive patch 404 is configured to apply external pressure from the rear of the sensor assembly 402 to maintain it in at a predetermined location on the subject 300, typically the thorax of the subject.

Figure 5:
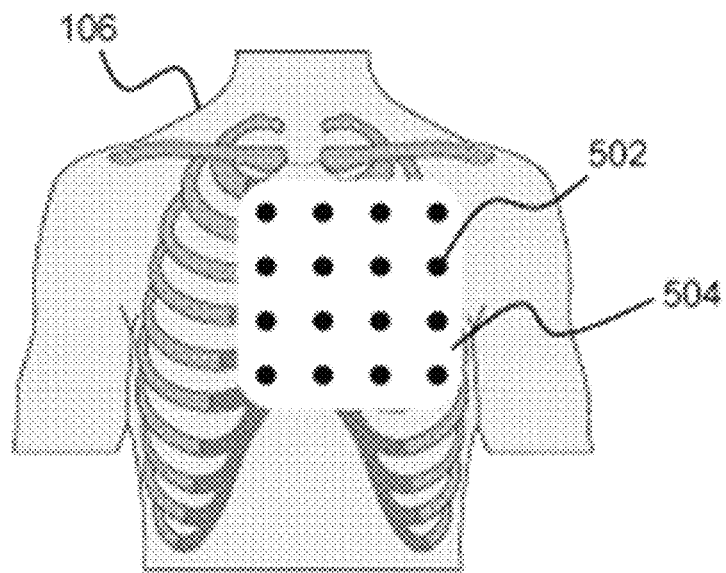

FIG. 5 shows a further arrangement in which a plurality of sensor assemblies 502 are fixed to the chest of the subject 300 with a common adhesive patch 504 configured to apply external pressure from the rear of the sensor assemblies 502 to maintain them in a predetermined location relative to the subject 300. Additionally or alternatively, the plurality of sensor assemblies 502 may be fixed to the back of the subject 300 in any suitable manner. By providing multiple sensor assemblies 502 around the torso of the subject, a force tomograph of the chest region may be generated from data derived from the sensors of the sensor assemblies 502.

Figure 6:
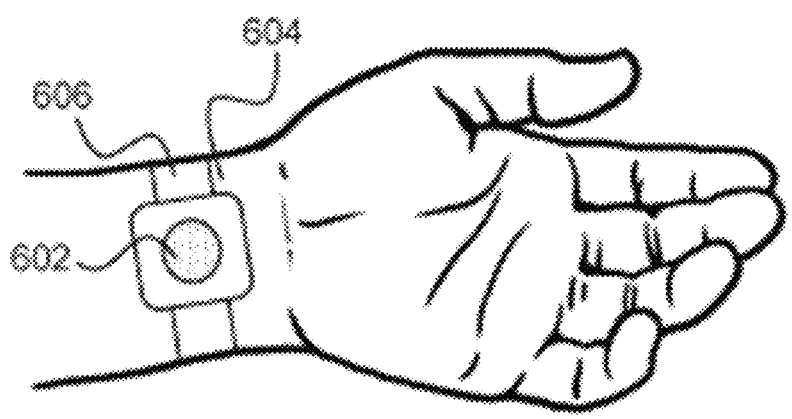

FIG. 6 shows a further arrangement in which a single sensor assembly 602 is fixed relative to a radial vein or artery located on the wrist 604 of the subject 300. The sensor assembly 602 may be held in place on the wrist 604 by a wrist strap 606 (or adhesive or other means) which also applies external force to the rear of the sensor assembly 602 to maintain contact between the assembly 602 and the wrist 606.

Figure 7:
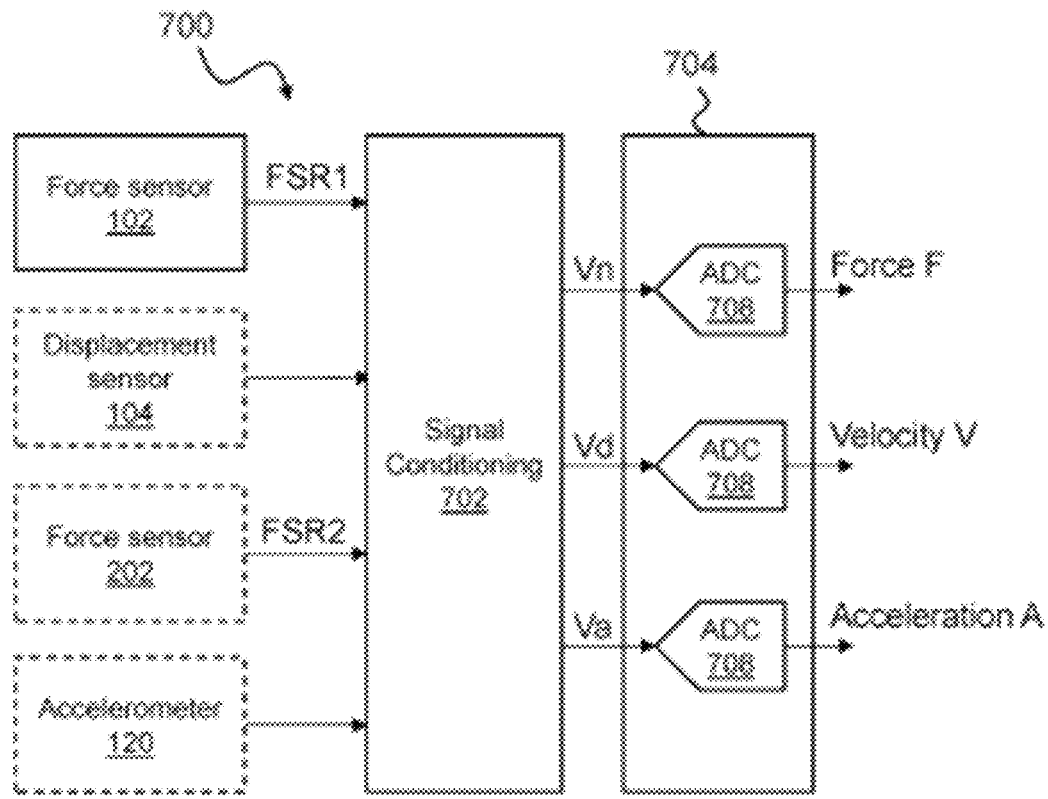
FIG. 7 shows a signal processing chain for processing signals received from a sensor assembly.
Figure 7:
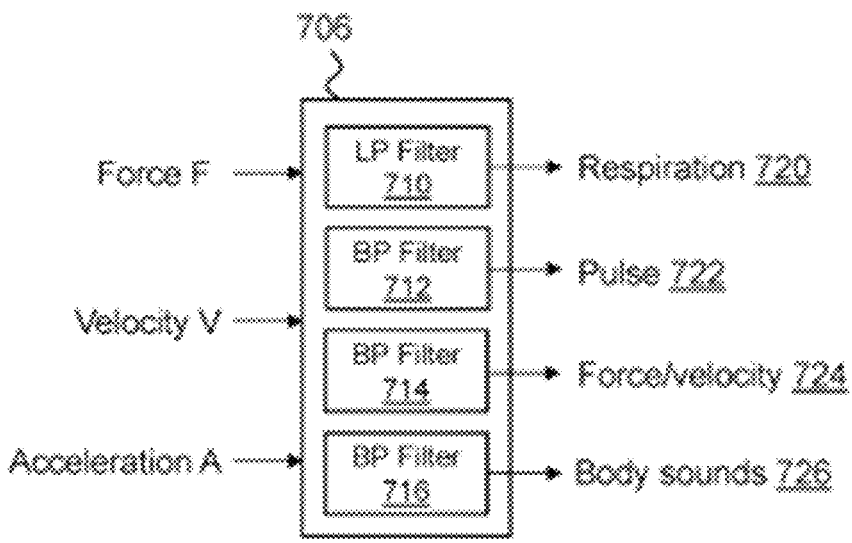

FIG. 7 is a block diagram illustrating an exemplary signal processing chain 700 for processing signals and/or variations in parameters of the force sensor 102, the displacement sensor 104, the second force sensor 202 and the optional accelerometer 120, generated from a living subject. In the following examples, the force sensor 102 and the second force sensor 202 will be described below as force-sensitive resistors (FSRs), FSR1 and FSR2, whose resistance is proportional to the force applied thereto. It will be appreciated, however, that embodiments are not limited to the use of FSRs as force sensors and other load cells or force sensors could be used in place of FSRs without departing from the scope of the present disclosure. Equally, in the following examples, the displacement sensor 104 will in some examples be described as a piezoelectric sensor, PZT, which generates a voltage in response to changes in displacement. Again, however, embodiments are not limited to the use of a piezoelectric sensor as the displacement sensor 104. Other exemplary displacement sensors include but are not limited to resistive, inductive, capacitive, eddy current, ultrasonic, magnetoresistive, and optical encoder displacement sensors.

The displacement sensor 104, the second force sensor 202, and the accelerometer 120 are shown in FIG. 7 in broken lines since some embodiments of the present disclosure require only the force sensor 102 for operation or the force sensor 102 and one or more of the displacement sensor 104, the second force sensor 202 and the accelerometer 120.

The signal processing chain 700 comprises a signal conditioning stage 702, an analogue-to-digital conversion stage 704 and filtering stage 706 to generate representations of one or more physiological parameters, including, but not limited to, respiration, blood ejection pulse, force parameters, velocity parameters, heart sounds, and blood pressure.

During the signal conditioning stage 702, a resistance FSR1 of the force sensor 102 is converted into an output voltage Vn either by hardware (processing circuitry) or by software in post processing.

Figure 8:
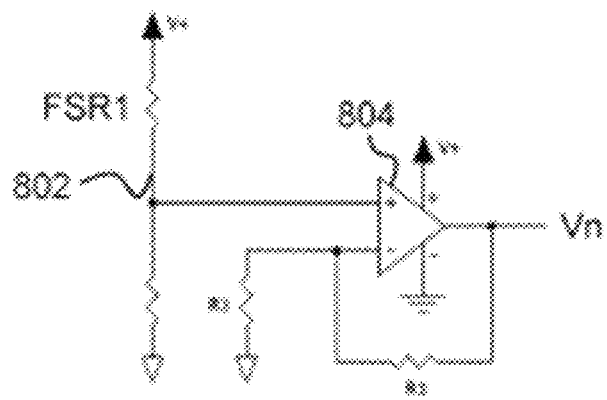
FIGS. 8 to 10 show example processing circuitry implemented by a signal conditioning stage of the signal processing chain of FIG. 7 for generating a force signal from a force sensor of the sensor assemblies of FIG. 1 or 2.
Figure 9:
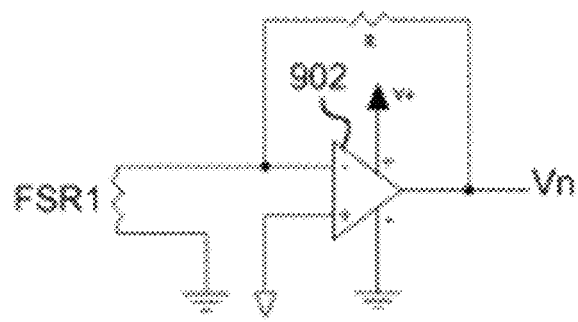
Figure 10:
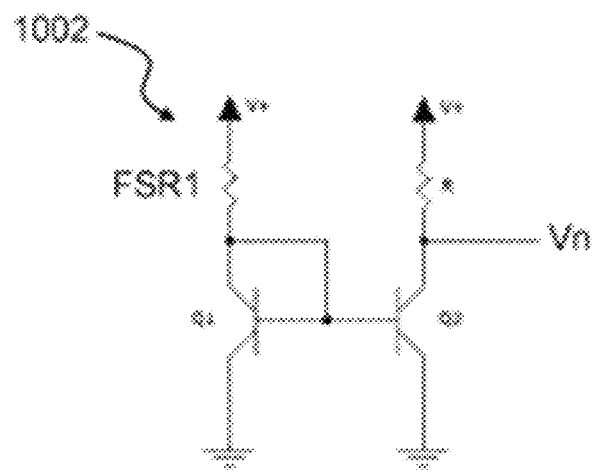

Exemplary hardware for performing such a conversion is shown in FIGS. 8 to 10. Referring to FIG. 8, the resistance FSR1 of the force sensor 102 forms one tail of a voltage divider 802, the output of which is provided to an input of a non-inverting amplifier 804 to produce an output voltage Vn proportional to the resistance FSR1 of the force sensor 102. In another embodiment, referring to FIG. 9, a change in resistance FSR1 of the force sensor 102 is converted using a trans-impedance amplifier 902, the resistance FSR1 configured as the variable input impedance of the amplifier 902. In a further embodiment, as shown in FIG. 10, the force sensor 102 is integrated into a current mirror 1002, the resistance FSR1 of the force sensor 102 configured as the biasing resistor of the current mirror 1002.

Figure 11:
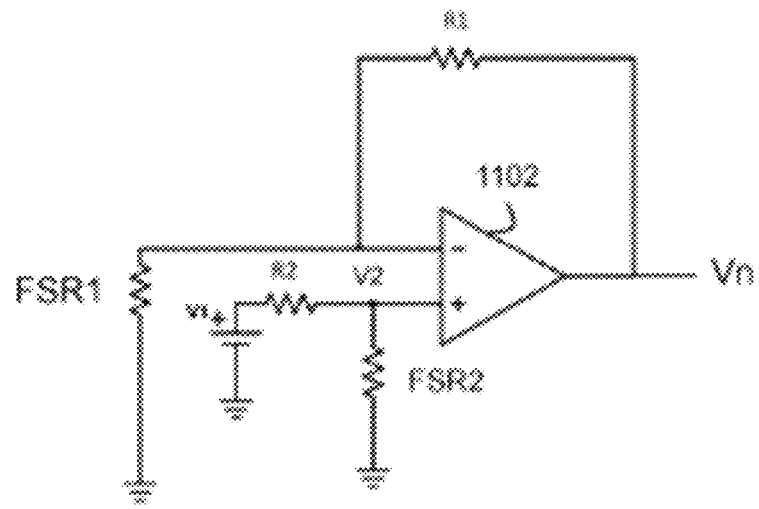
FIGS. 11 to 13 show circuit diagrams of example processing circuitry implemented by a signal conditioning stage of the signal processing chain of FIG. 7 for generating a force signal based on characteristics of the force sensor and second force sensor of the sensor assemblies of FIG. 2.
Figure 12:
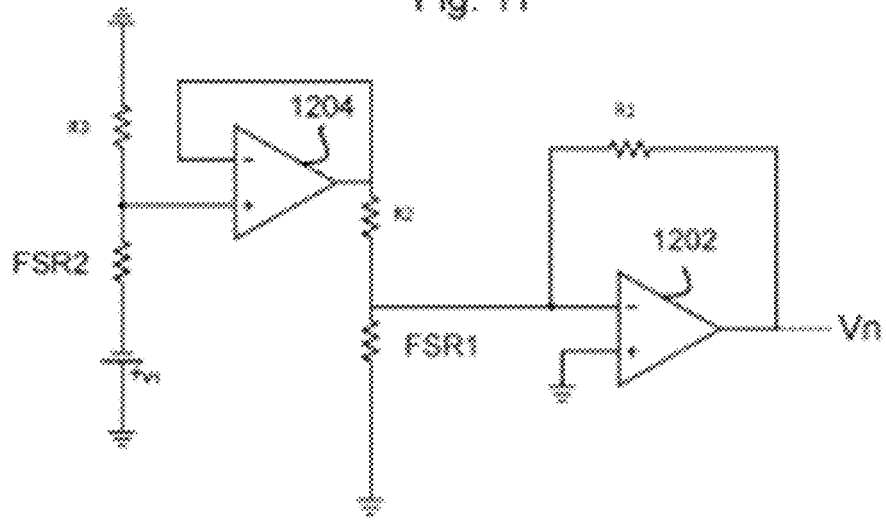
Figure 13:
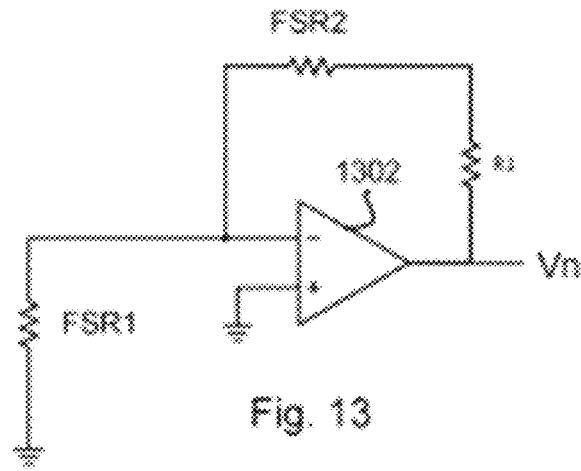

As described above, the second force sensor 202 may be used to calibrate for varying force applied to the rear (non-subject facing) side of the sensor assembly 200 by any fixing device or the subject itself. Referring again to FIG. 7, signal conditioning circuitry is implemented during signal conditioning 702 to further bias the resistance of the force sensor 102 based on a resistance FSR2 of the second force sensor 202. FIGS. 11 to 13 each illustrate an example of a hardware layout suitable for such function.

FIG. 11 is a variation of the trans-impedance amplifier arrangement of FIG. 9 with a biasing voltage V2 coupled to a non-inverting input of an amplifier 1102, the biasing voltage V2 being varied by the current sink through the resistance FSR2 of the second force sensor 202.

FIG. 12 shows a further variation of the arrangement of FIG. 9 comprising a trans-impedance stage 1202 with a further stage 1204 configured to inject into the inverting input of stage 1202 current proportional to the resistance FSR2 of the second force sensor 202, thus reducing the output voltage Vn as resistance FSR2 increases. The value of the DC voltage V1 and the passive resistors R1 and R2 in both FIGS. 11 and 12 are set according to the power supply used and the desired dynamic range of the output voltage Vn.

FIG. 13 shows a further variation in which the resistance FSR2 of the second force sensor 202 is provided in the feedback loop of a trans-impedance stage 1302. The gain of the stage 1302 is proportional to the resistance FSR2 and thus the pressure applied to the rear surface of the sensor assembly 200. Again, the resistance R1 is set according to the power supply used and the desired dynamic range of the output voltage Vn.

It will be appreciated that any of the above hardware solutions may alternatively be implemented in software, either in real time or after recording of signals from two or more of the sensors 102, 104, 202.

It will be also appreciated that, in addition to calibrating the first sensor 102, signals derived from the first sensor 102 can be used to determine flesh compliance, e.g. to distinguish between tissues (fat/muscle percentages etc.). Such measurements may be used to determine an amount of fat under the skin of a subject.

As described above, in some embodiments, the displacement sensor 104 comprises a piezoelectric sensor configured to generate a current in response to a change in displacement. In such cases, the DC offset and AC voltage swing of the signal output form the displacement sensor 104 may need to be adjusted or calibrated. To do so, the signal conditioning stage 702 conditions the signal output from the displacement sensor 104 by implementing process circuitry such as that shown in FIGS. 14, 15a and 15b.

Figure 14:
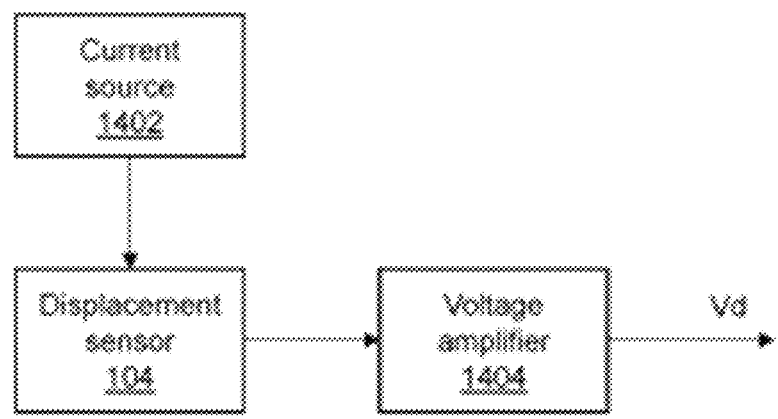
FIG. 14 shows block diagram of example processing chain implemented by a signal conditioning stage of the signal processing chain of FIG. 7 for generating a conditioned velocity signal from the displacement sensor of the sensor assemblies of FIG. 1a or 1b.

Referring to FIG. 14, the displacement sensor 104 (PZT) is polarized using a current source 1402 (which may be digitally controlled) to adjust the AC voltage swing due to changes in displacement. A subsequent voltage amplifier 1404 is provided for adjustment of DC offset.

Figure 15A:
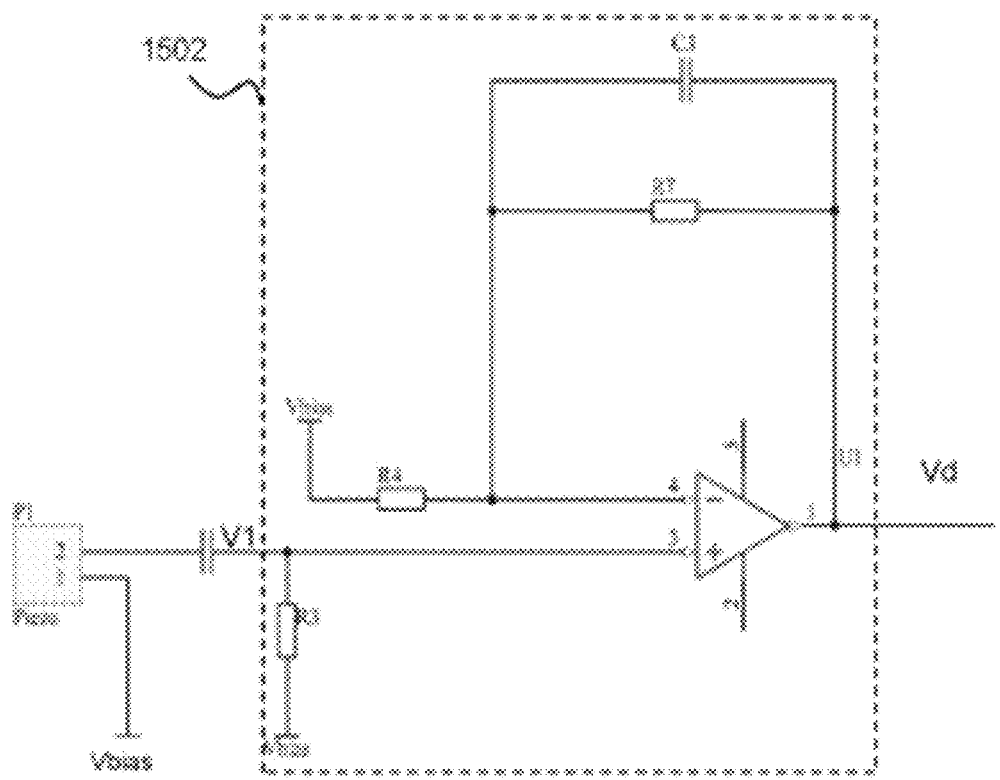
FIG. 15a shows a first embodiment of processing circuitry implemented by a signal conditioning stage of the signal processing chain of FIG. 7 for generating a conditioned velocity signal from the displacement sensor of the sensor assemblies of FIG. 1a or 1b.

FIG. 15a shows an exemplary implementation of signal conditioning 702 for the displacement sensor 104. As with FIG. 14, current is injected into the displacement sensor 104 and the resultant high pass filtered signal V1 provided to a voltage amplifier stage 1502 to adjust DC offset. It is noted that feedback resistance R7 and input impedance R3 of the non-inverting input of the amplifier stage 1502 are chosen to match the impendence of the displacement sensor 104 (PZT).

Figure 15B:
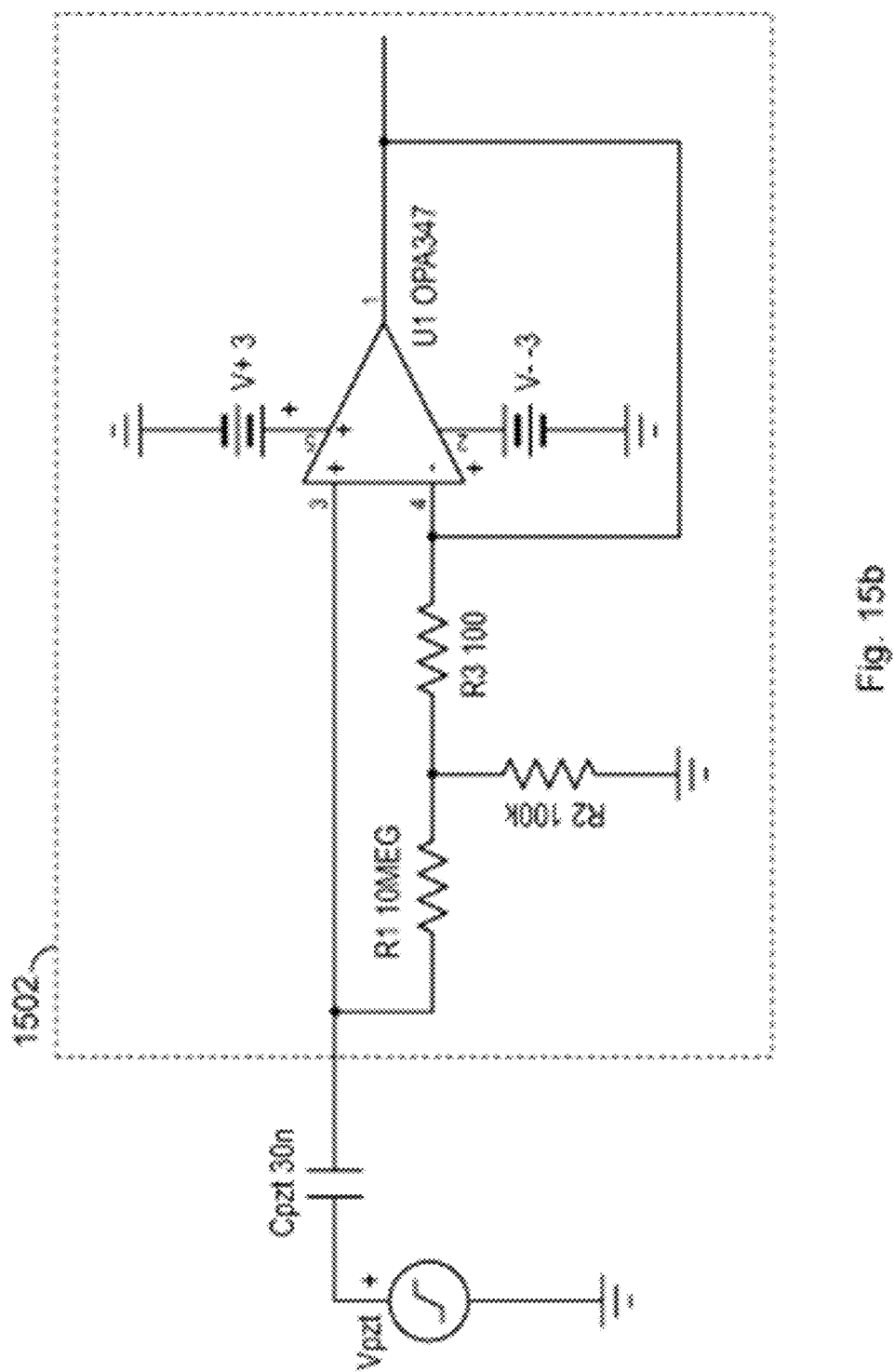
FIG. 15b shows a second embodiment of processing circuitry implemented by a signal conditioning stage of the signal processing chain of FIG. 7 for generating a conditioned velocity signal from the displacement sensor of the sensor assemblies of FIG. 1a or 1b.

FIG. 15b shows another exemplary implementation of signal conditioning circuitry 1502 for the displacement sensor 104. With reference to FIG. 15a of the drawings, like reference numerals refer to like parts unless otherwise specified. This signal conditioning circuitry 1502 exploits Miller's theorem to increase the input impedance ($R_{IN}$) detected by the displacement sensor 104 based on the following equations:

$$R_{IN} = R_1 \left(1 + \frac{R_2}{R_3}\right)$$

$$f_{3dR} = \frac{1}{2\pi R_{IN} C_{PZT}}$$

This improves the overall low-frequency response of the signal conditioning circuitry 1502 by reducing the high-pass cut-off frequency which is selected to reduce the possible phase-shift introduced by the high-pass response, even at the lowest frequencies of interest, being the lower limit of the respiratory signals band to assist in comparison with the signals from the force sensor 102. In some applications, the cut-off frequency is to be set to a range of about 0.01-0.05 Hz.

To be able to use different displacement sensors 104 without the need for bespoke circuitry, the signal conditioning circuitry 1502 may be tunable based on the particular capacitance of the selected displacement sensor 104. Using surface mounted device (SMD) resistors in a bootstrapping configuration, smaller resistance values can be employed reducing the cost of the circuitry 1502. As an example, a resistor R1 of 100 MΩ, a resistor R3 of 100Ω and a trimmer, R2, of 100 kΩ could be used in circuit 1502 so that an impedance $R_{IN}$ of 100 MΩ is "seen" by the displacement sensor 104 when R2 is set to 0 (to provide a cut-off frequency of 0.05 Hz for a displacement sensor 104 capacitance of 30 nF). $R_{IN}$ could be increased to $10^{11}$Ω by increasing the trimmer resistance by adjusting R2.

Referring again to FIG. 7, during the signal conditioning stage 702 a conditioned force signal Vn representing the force applied to the coupler 106 and a conditioned displacement signal Vd representing the displacement velocity at the coupler 106 are generated. Optionally, an acceleration signal Va representing acceleration at the coupler 106 may also be generated. These analogue signals are then converted to digital representations of force F, displacement velocity V, and acceleration A, respectively, by an analogue-to-digital conversion (ADC) stage 704 using one or more ADCs 708. In some embodiments a single ADC 708 may be provided, the conditioned signals Vn, Vd, Va provided to the ADC via a multiplexer (not shown). In other embodiments, the conditioned signals Vn, Vd, Va may be provided to separate ADCs 708 as shown in FIG. 7.

Digital signals F, V, A are then provided to a digital filter stage 706 configured to implement one or more filters 710, 712, 714, 716 to filter the force, velocity and (optional) accelerometer signals F, V, A to generate one or more outputs representative of physiological parameters of the subject. Such parameters are specific to the location on a living subject at which the assemblies 100, 200 are located during measurement. For example, when positioned at locations on the thorax of a subject as shown in FIGS. 3 to 5, the digital filter stage 706 is operable to extract data pertaining to cardiac activity (e.g. seizmocardiography, heart sounds etc.) in addition to respiration, and pulse cardiography. With the assemblies 100, 200 positioned on the wrist, the digital filter stage 706 may only be able to extract data pertaining to respiration and blood pulse.

A respiration signal 720 from the subject is extracted by low pass filtering the force signal F using a low pass filter 710. The low pass filter 710 may, for example, have a low pass threshold of about 0.5 Hz.

A pulse signal is generated from the force signal by band pass filtering the force signal F with a band pass filter 712, The band pass filter may, for example, have a passband of between about 0.5 Hz and about 8 Hz.

Force and velocity parameters specific to the organ of the living subject being monitored are extracted from each of the force and velocity signals F, V, respectively, by band pass filtering the signals F, V with a further band pass filter 714. For force and velocity parameters of the heart, for example, the band pass filter 714 may have a passband of between about 8 Hz and about 40 Hz.

Body sounds are also able to be extracted from the force and velocity signals F, V using a band pass filter 716 having a lower threshold of about 20 Hz, about 30 Hz, about 40 Hz, or about 50 Hz in combination with an upper threshold of about 150 Hz, about 200 Hz, about Hz, about 250 Hz, or about 300 Hz. In some embodiments, the band pass filter 716 may have a passband of between about 40 Hz and about 300 Hz. Depending on the position of the sensor assembly 100, 200, the body sounds may comprise one or more of heart sounds (e.g. rushing blood, valve movement), gut sounds (e.g. gas displacement), respiration, snoring, swallowing and foetal sounds (including foetal movement, foetal heart sounds, foetal respiration, foetal gas displacement etc.), muscle contraction around airways, such as the trachea.

Size reduction in airways may also be monitored by monitoring changes in sounds emanating from the neck region. For example, wheezing or higher pitched sound or vibrations at the neck may be indicative of hypopnoeas (partial reduction in breathing), apnoeas, or asthma and other pulmonary and respiratory conditions. As discussed below with reference to FIG. 23, body sounds may also be extracted from signals received from the accelerometer 120. Body sounds may be generated on the basis of a combination of two or more of the force, velocity and acceleration signals F, V, A.

Extracted body sounds may be output to one or more speakers or headsets to be heard by a clinician. As such, the sensor assemblies 100, 200 may act as digital stethoscopes providing a high resolution digital representation of body sounds. Such extracted body sounds can be modulated and/or shifted in frequency to be more easily heard by the human ear. For example, extracted body sounds may be shifted in frequency into the centre of the human hearing range.

Figure 16:
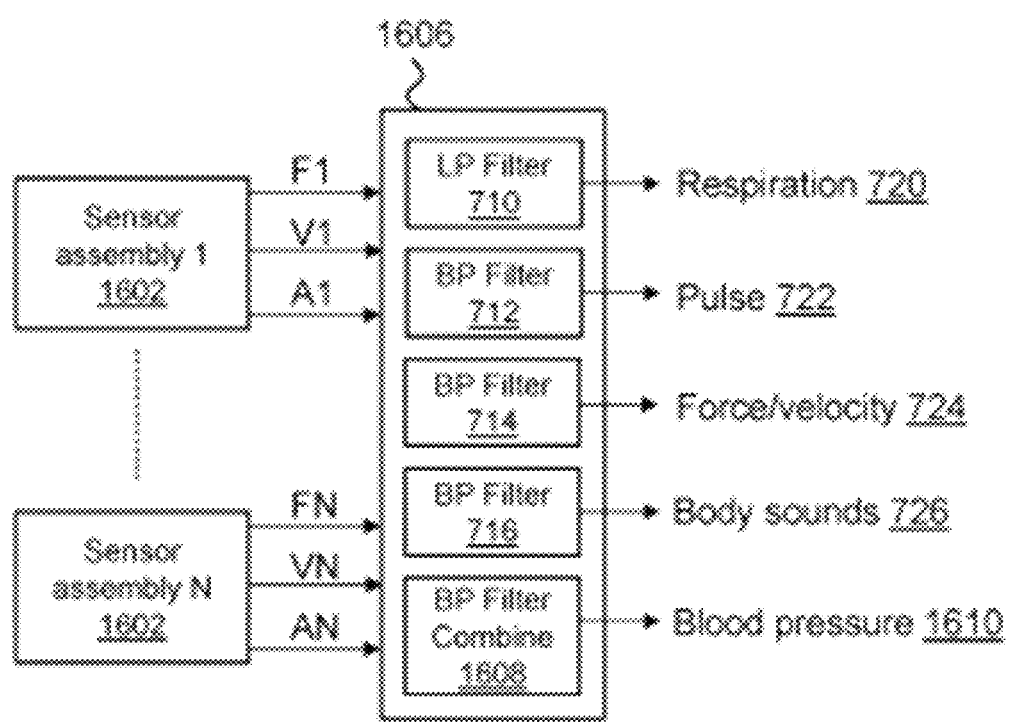
FIG. 16 shows a signal processing chain for processing signals received from multiple sensor assemblies.

It is noted that the various filters 710, 712, 714, 716 of the digital filter stage 706 are provided only as examples of filters which may be implemented to extract information from the force and velocity signals F, V. One or more of the filters 710, 712, 714, 716, 718 may be omitted or other filters added depending on the physiological parameters to be extracted and the location(s) of the assembly(s) 100, 200 on the subject.

Where multiple sensor assemblies are provided at different locations on the subject, each of the force, velocity and accelerometer signals generated from such assemblies may be filtered in a similar manner to that described above with reference to FIG. 7. For example, as shown in FIG. 16 in which like reference numerals refer to like parts, digital force, velocity and acceleration signals F1-FN, V1-VN, A1-AN, respectively, may be provided from N sensors assemblies 1602, 1604 to a digital filter stage 1606. For simplicity, the sensor assemblies 1602, 1604 include signal conditioning and A/D conversion circuitry for generating the force, velocity and acceleration signals.

In addition to filtering individual force and velocity signals from one or more of the sensor assemblies 1602, 1604, the digital filter bank 1606 is also configured to combine force and/or velocity signals from two or more of the sensor assemblies 1602, 1604 either before or after filtering. For example, the filter bank 1606 may comprise a bandpass filter and combine module 1608 configured to combine force signals F1, FN from two of the sensor assemblies 1602, 1604 positioned at different locations on the subject to generate a blood pressure signal 1610. The signals F1, FN may be band pass filtered before being combined or the signals may be combined and the band pass filter applied to the combined signal to generate the blood pressure signal 1610.

The filter bank 1606 is configured to combine any combination of signals received before or after filtering in any manner without departing from the scope of the present disclosure.

Having regard to the above, FIGS. 17 to 25 graphically illustrate various signals extracted by exemplary sensor assemblies 100, 200 fixed at various locations on a human subject.

Figure 17:
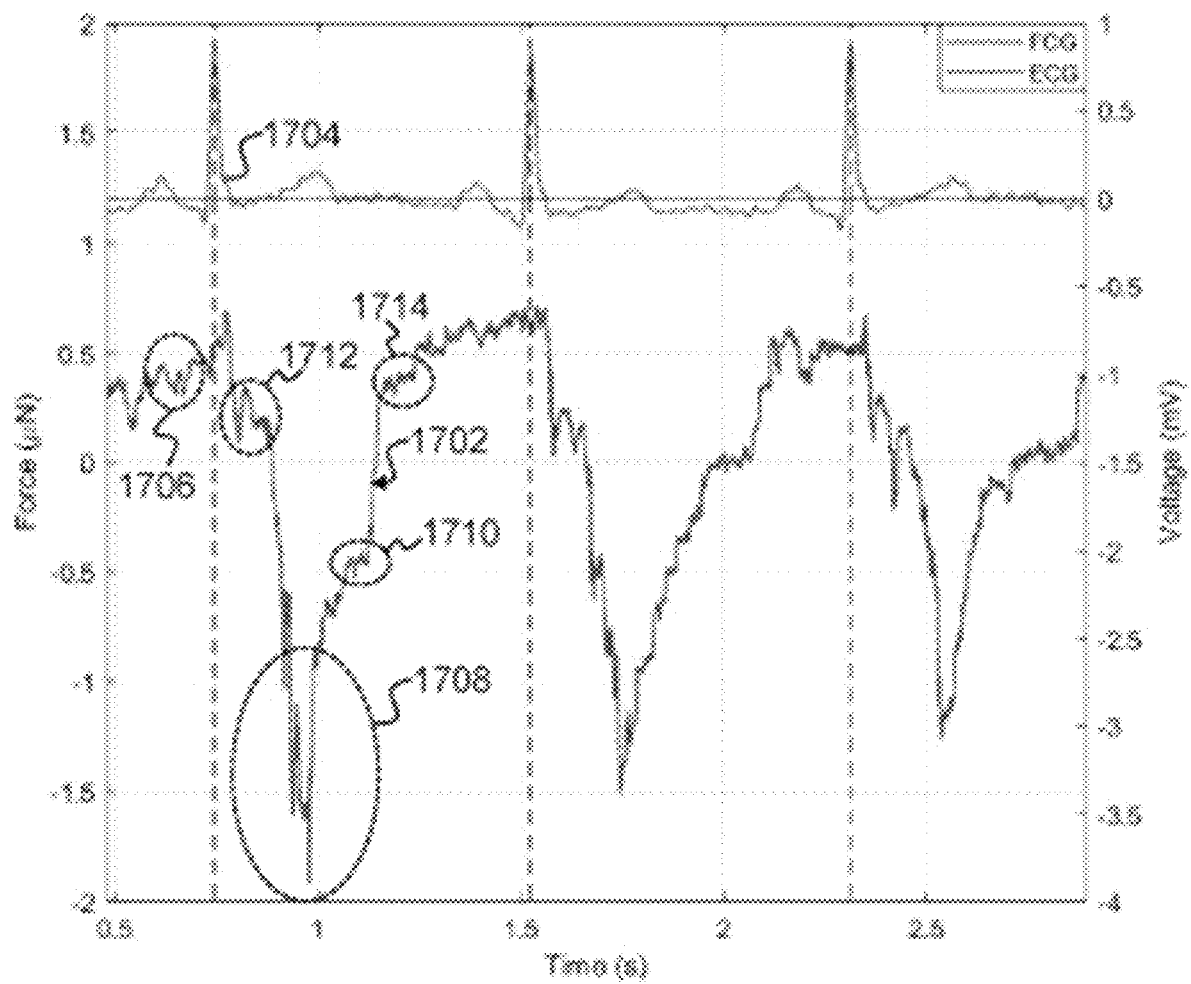
FIG. 17 is a plot showing force versus time recorded by the sensor assembly of FIG. 1a positioned on the sternum of a subject as shown in FIG. 3.

FIG. 17 graphically illustrates an extracted force signal 1702 acquired from the sensor assembly 300 of FIG. 3 positioned on the sternum of the subject 300 and secured by the belt 304, at the xiphoid process. A corresponding ECG signal 1704 measured simultaneously is also shown for comparison. It can be seen that various cardiac parameters can be identified in the force signal 1702, including but not limited to a P-wave component 1706, a QRS complex 1708, and a T-wave component 1710. As such, the sensor assembly 300 may be used in the diagnosis of diseases such as arrhythmias (e.g. atrial fibrillation). Additional parameters can also be extracted from this force signal 1702 including duration of each phase of the cardiac cycle, heart valve opening and closure times 1712, 1714, heart contractility level, stroke volume, cardiac output, and pulse transit time.

Figure 18:
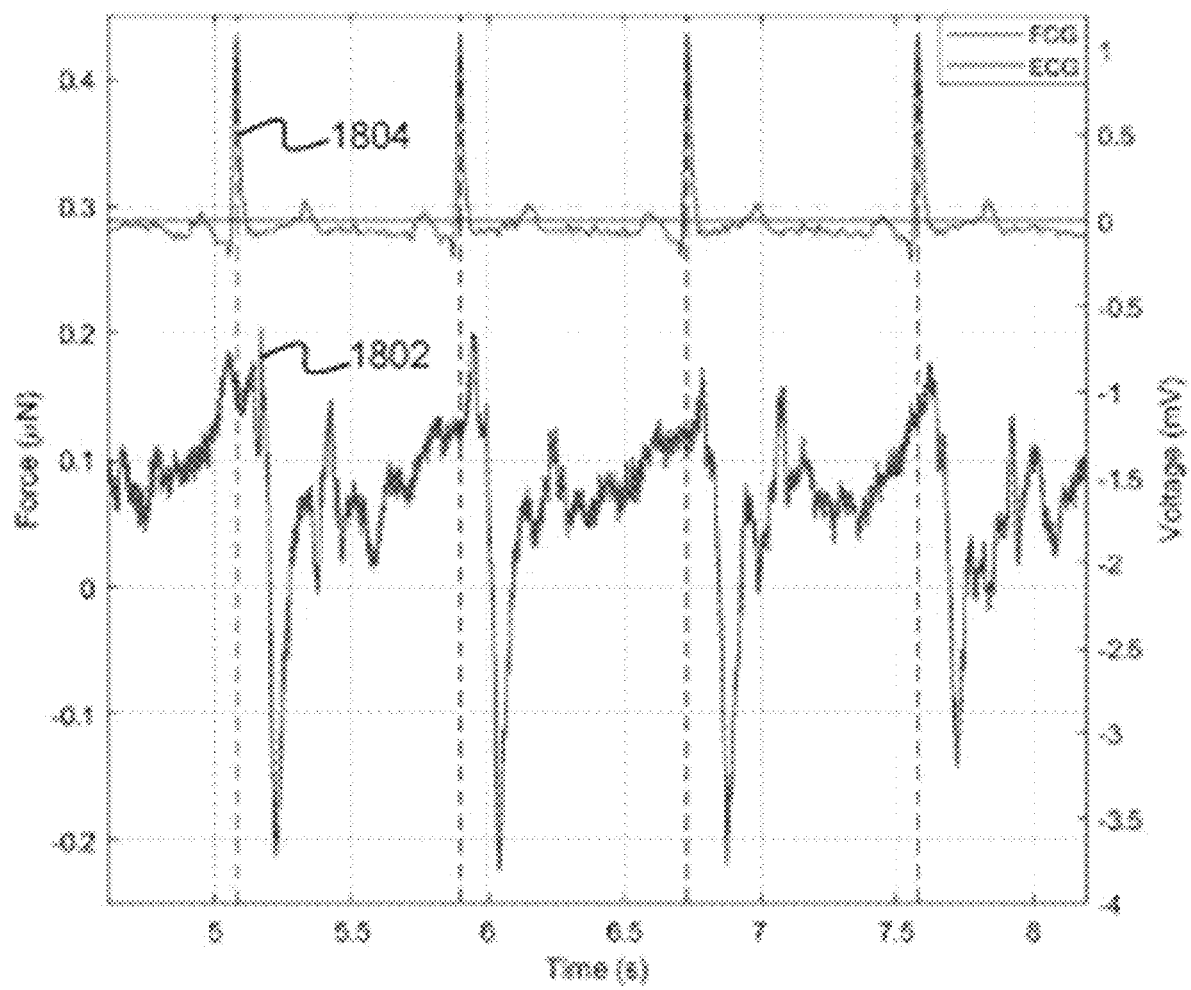
FIG. 18 is a plot showing force versus time recorded by the sensor assembly of FIG. 1a positioned on the sternum of a subject as shown in FIG. 3.

FIG. 18 graphically illustrates an extracted force signal 1802 acquired from a sensor assembly similar to that shown in FIG. 3 positioned in a similar location with an adhesive patch instead of the belt 304, at or near the xiphoid process. A corresponding ECG signal 1804 measured simultaneously is also shown for comparison. It can be seen that, similar to FIG. 17, the force signal 1802 provides various cardiac indications corresponding to those of the ECG signal 1804.

Figure 19:
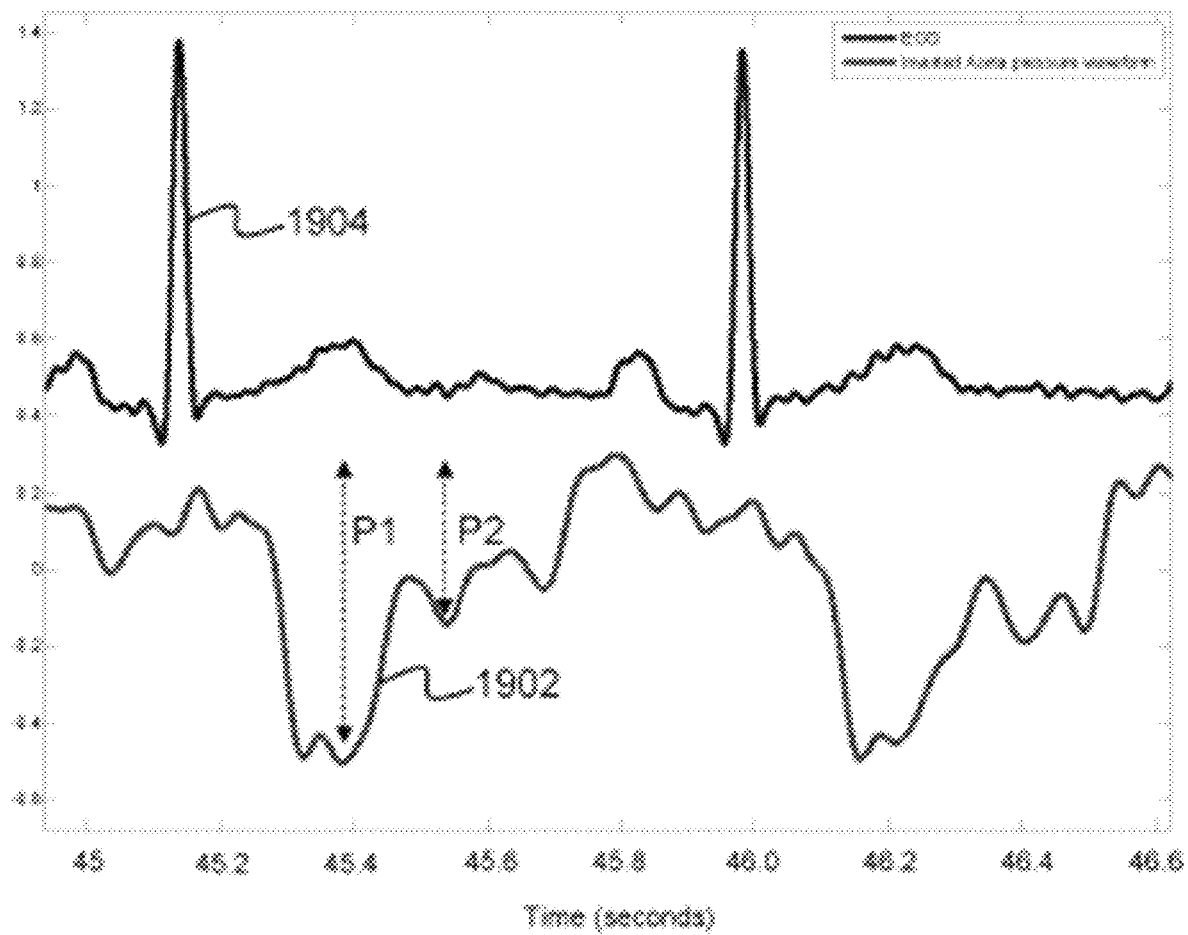
FIG. 19 is a plot of the sum of two force signals from force sensors of sensor assemblies respectively located at a suprasternal notch and a cardiac apex of a subject.

FIG. 19 graphically illustrates a combined signal 1902 which is the sum of force signals generated by force sensors of the sensor assemblies 402 shown in FIG. 4, one of the sensor assemblies 404 placed on the upper thorax at or near the suprasternal notch, the other of the sensor assemblies 402 placed on the lower thorax at or near the cardiac apex. A corresponding ECG signal 1904 is also provided for reference. It can be seen that the resultant combined signal 1902 represents an estimate of central arterial pressure through the heart, from which various parameters can be estimated, including the peak reflected and ejected waves P1, P2. It will be appreciated, therefore that differential measurements of force and/or velocity using sensor assemblies described herein enable determination of blood pressure gradients between various parts of a subject, not only central arterial pressure. For example, measurements of force and/or velocity using two or more sensor assemblies at the suprasternal notch and the femoral artery (or subclavian artery or other peripheral artery) may be compared to determine a peripheral blood pressure.

Figure 20:
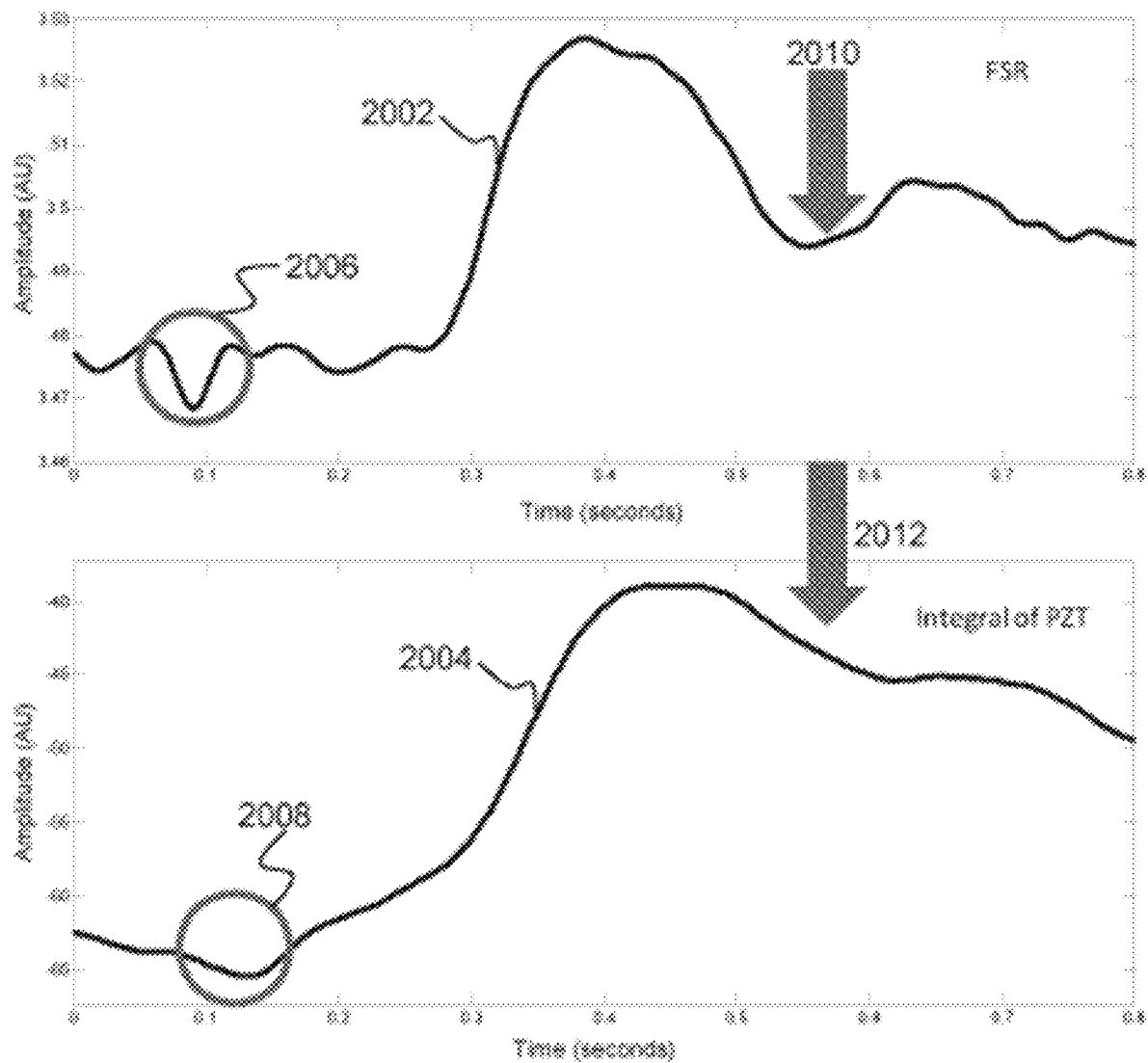
FIG. 20 is a plot comparing a force signal derived from a force sensor of the sensor assembly of FIG. 1a and the integral of a displacement velocity signal derived from a displacement sensor of the sensor assembly of FIG. 1.

FIG. 20 graphically illustrates a force signal 2002 generated from the force sensor 102 (FSR) of the sensor assembly 100 and the integral signal 2004 of a displacement velocity signal generated from the displacement sensor 104 (PZT) of the sensor assembly 100 positioned at or near the xiphoid process as shown in FIG. 3. This figure illustrates the substantial resemblance of the integral 2004 of the velocity signal and the force signal 2002, the velocity being the P t order derivative of force displacement. It can therefore be seen that the force signal 2002 can be used to calibrate the velocity signal 2004 either before operation of the sensor or in real time during monitoring to account for sensor drift, particularly when using a piezoelectric sensor. It can also be seen from FIG. 20 that the P-wave is visible in both the force signal 2002 and the integral signal 2004, highlighted by respective circles 2006, 2008 in the plots. Additionally, the dicrotic notch can also be seen in both signals 2002, 2004, highlighted by the large arrows 2010, 2012 in each plot in FIG. 20.

Figure 21:
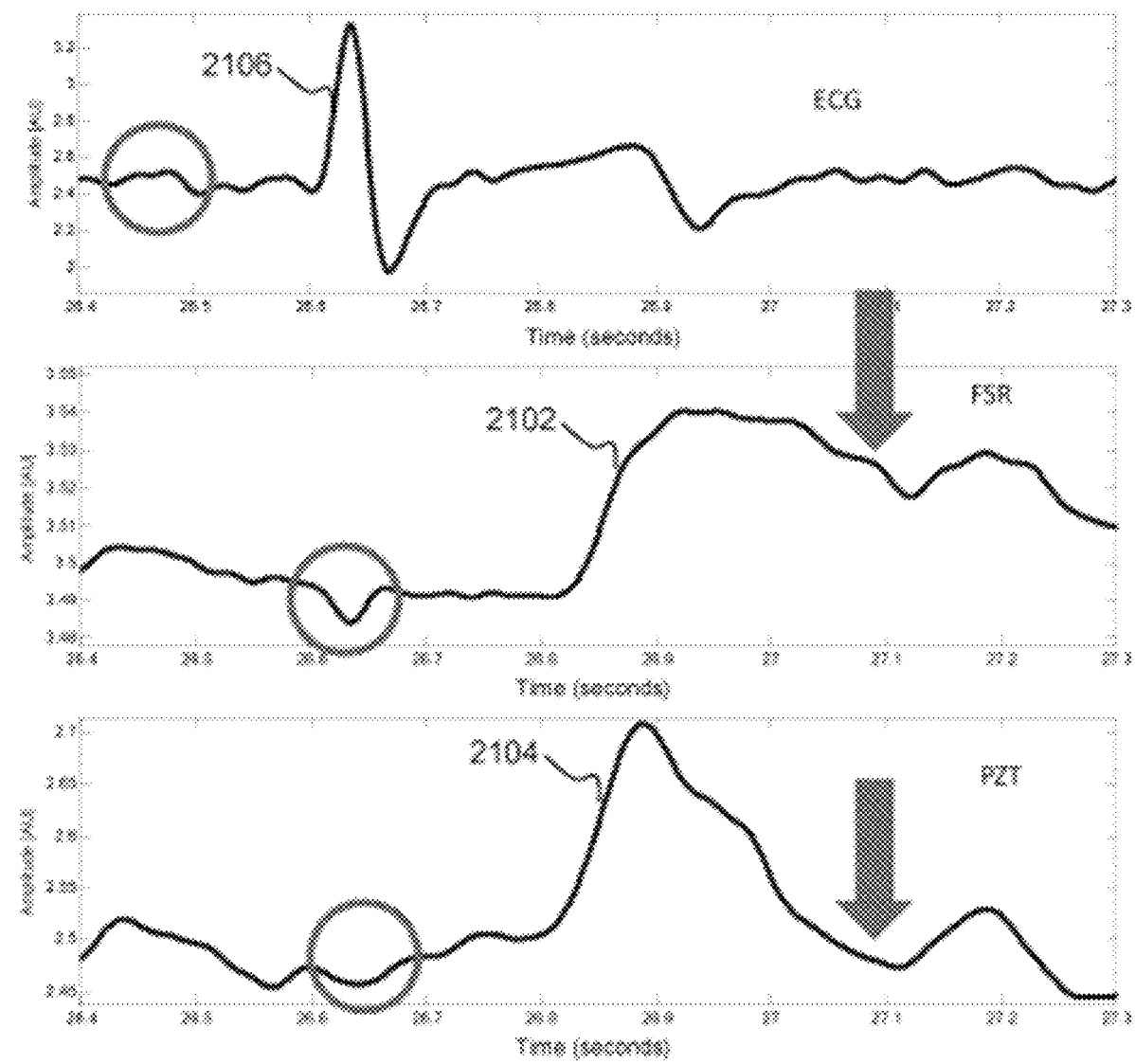
FIG. 21 is a plot comparing an electrocardiogram (ECG) with a force signal and a displacement signal derived from the sensor assembly of FIG. 1.

FIG. 21 graphically illustrates a force signal 2102 generated from a force sensor (FSR) and a displacement velocity signal 2104 generated from a displacement sensor (PZT) of the sensor assembly 602 positioned on the wrist 604 of the subject 300 at or near the radial artery as shown in FIG. 6. A corresponding ECG signal 2106 is also shown for comparison. Circles in each of the plots highlight the measured p-wave visible in each signal 2102, 2104, 2106. Large arrows identify the dicrotic notch in each of the force and velocity signals 2102, 2104. It can be seen from FIG. 20 that the p-wave is visible from signals received from the force and velocity signals 2102, 2104 measured at the wrist 604.

Figure 22:
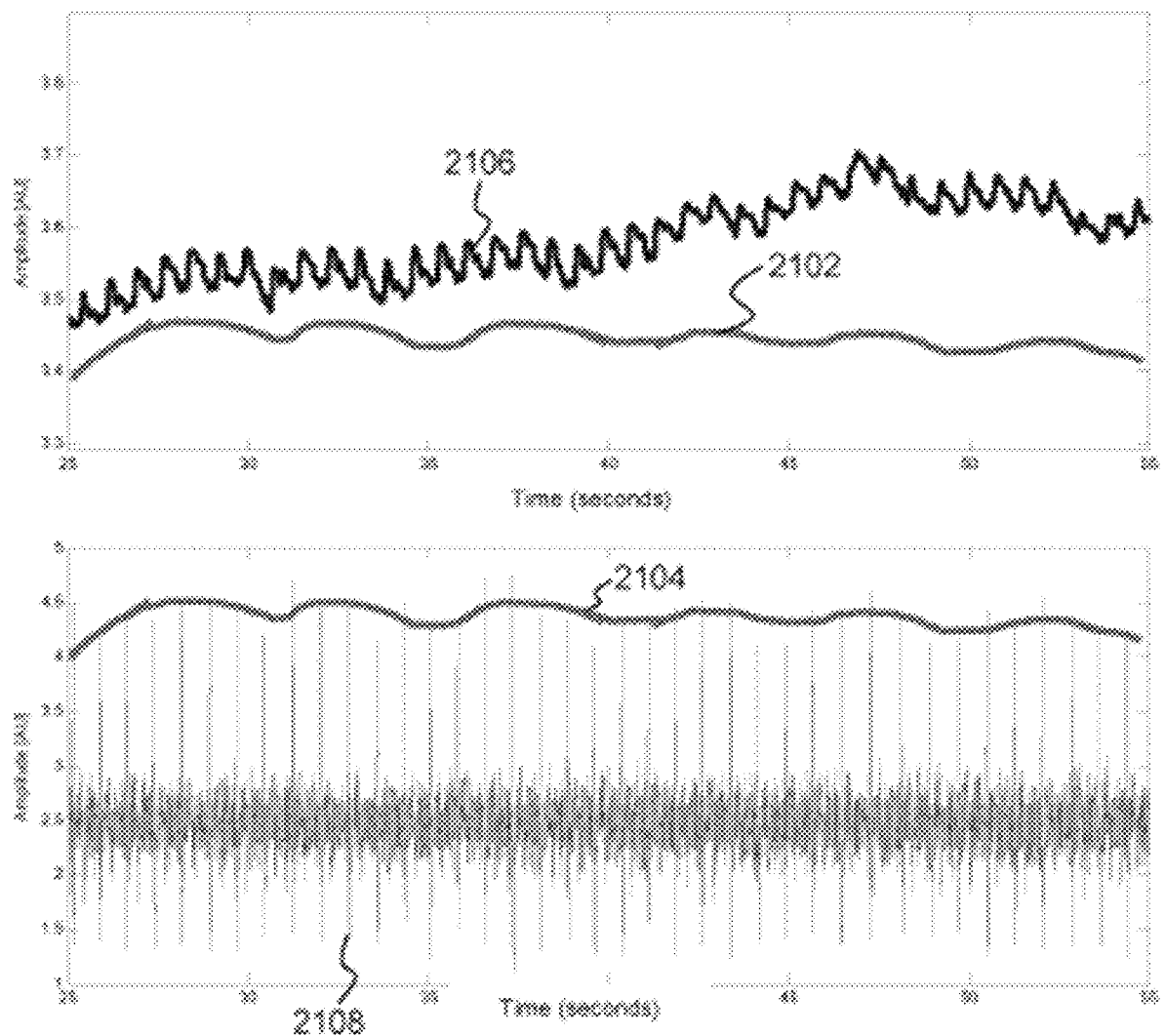
FIG. 22 is a plot showing a force signal derived from a force sensor of the sensor assembly of FIG. 1a and a respiration signal derived from the force signal alongside an ECG and a respiration signal derived from the ECG.

FIG. 22 graphically illustrates an extraction of respiration signals 2102, 2104 from respective force and ECG signals 2106, 2108 by low pass filtering, for example using the low pass filter 710 described above with reference to FIG. 7.

Figure 23:
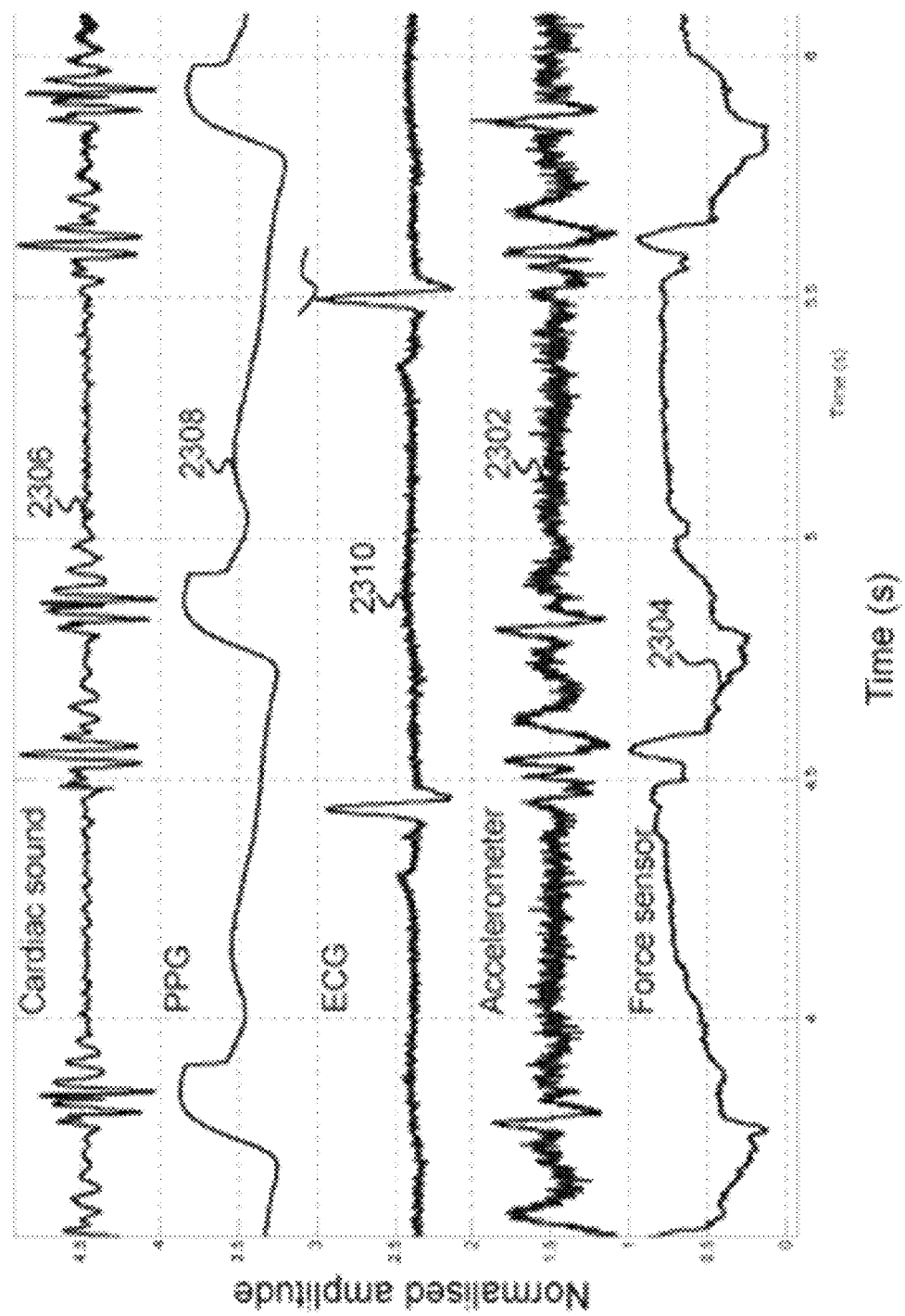
FIG. 23 is a plot showing force and accelerometer signals derived from the sensor assembly of FIG. 1a alongside a cardiac sound signal, an ECG and a photophethysmogram (PPG)

As mentioned above, the sensor assemblies 100, 200 may be provided with one or more accelerometers configured to measure acceleration of the sensor assemblies 100, 200. FIG. 23 graphically illustrates an accelerometer signal 2302 derived from the accelerometer 120 and a force signal 2304 derived from the force sensor 102 of the sensor assembly 100 positioned at or near the xiphoid process as shown in FIG. 3. For comparison, recorded cardiac sound 2306, photoplethysmogram (PPG) 2308 and ECG 2310 signals are also shown. It can be seen from this figure that the signal 2302 received at the accelerometer 120 has similar characteristics to the recorded cardiac sound signal 2306 having similar features. As such, it can be seen that the accelerometer 2302 is able to be used to generate sound signals representing body sounds as is described above with reference to FIG. 7.

Figure 24:
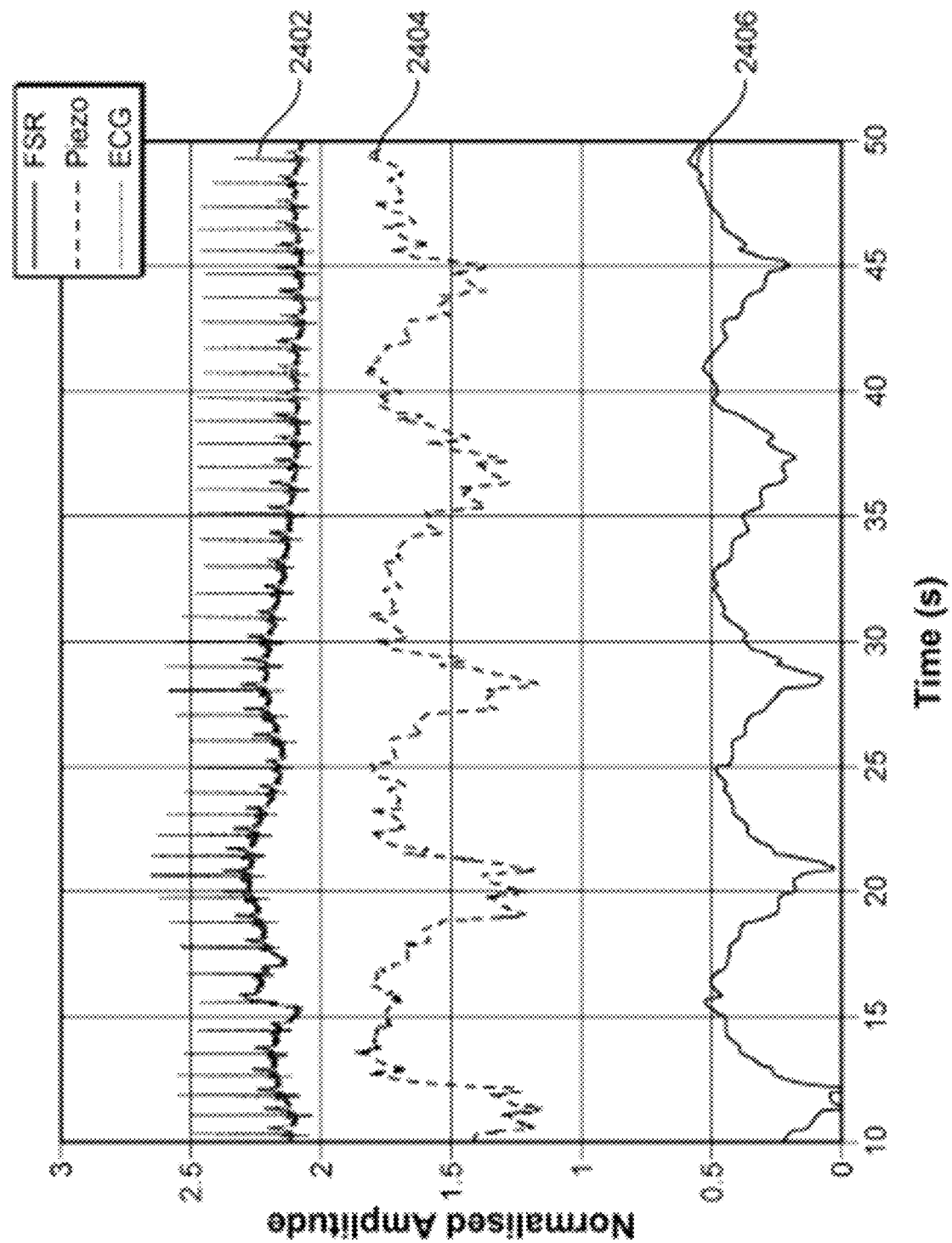

FIG. 24 graphically illustrates the raw data extracted from the sensor assembly 100 of FIG. 1a. In FIG. 24, an ECG signal 2402 is provided for reference, trace 2404 shows five cycles of respiration as recorded by the displacement sensor 104 and trace 2406 shows five cycles of respiration as recorded by the force sensor 102.

Figure 25:
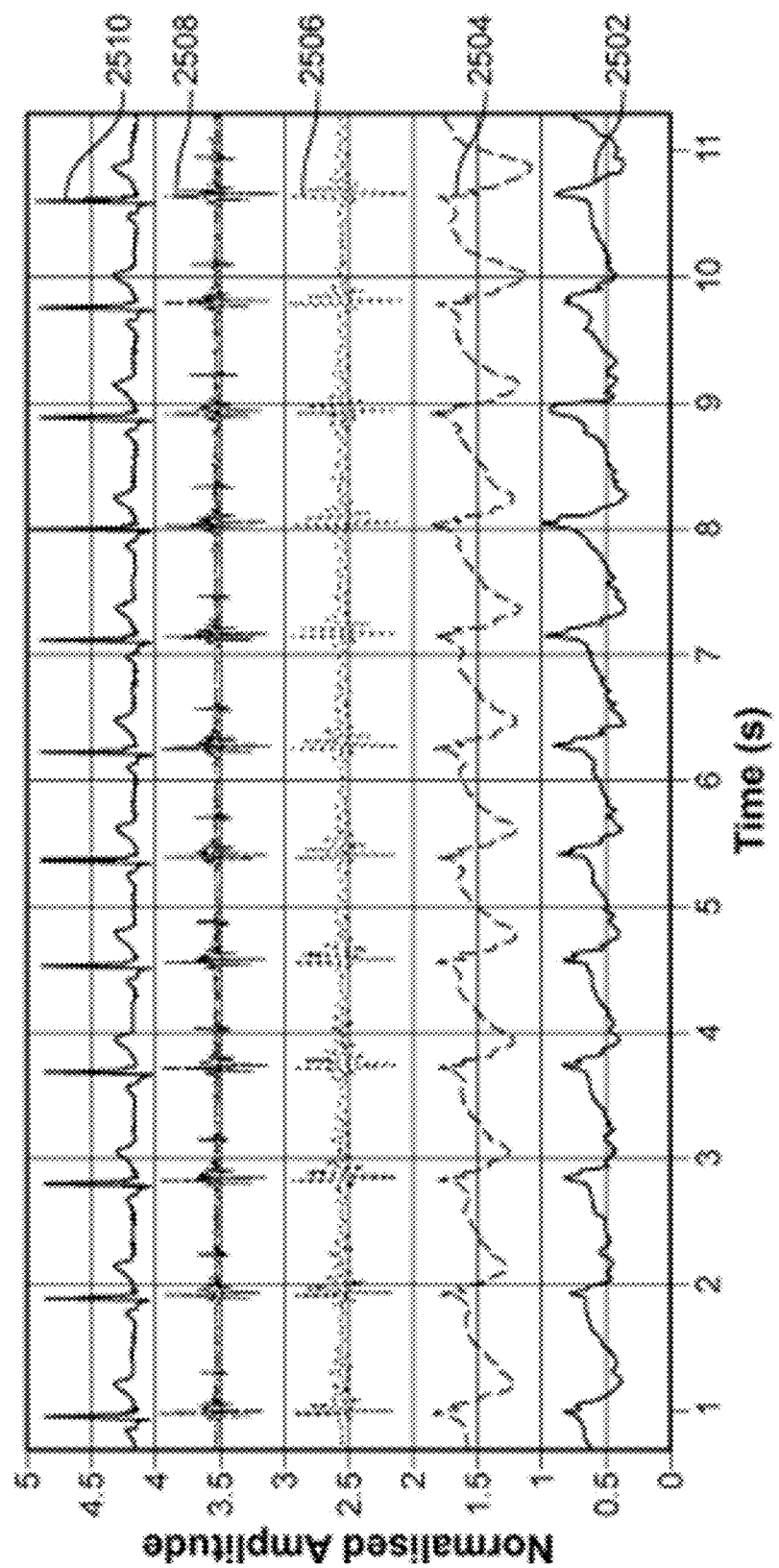

Similar to FIG. 23, FIG. 25 graphically illustrates data of sounds and a seismocardiogram extracted from the sensor assembly 100 of FIG. 1a. In FIG. 25, trace 2502 represents the raw data from the force sensor 102 after respiration artefacts have been filtered from the signal and trace 2504 represents the raw data from the displacement sensor 104 after removal of respiration artefacts. Trace 2506 is a seismocardiogram extracted from the displacement sensor 104 using the signal conditioning circuitry of FIG. 7. Trace 2508 is a sound plot extracted from the displacement sensor 104. Trace 2510 is an ECG signal provided for comparison purposes. It can thus be seen that, by suitable signal conditioning, signals can be extracted from the displacement sensor 104 representing body sounds and providing a seismocardiogram without the need for ECG equipment. Thus a subject wearing the sensor assemblies 100, 200 is able to be monitored while carrying out activities and need not wait for completion of the activities to have ECG equipment attached to the subject's body.

FIGS. 26 and 27 are respective cross-sectional and plan views of a sensor assembly 2300 comprising a flexible sensor 2302 at least partially encapsulated in a flexible carrier layer 2304. Like the force sensor 102 of the assembly 100 of FIG. 1a, the force sensor 2302 may be an FSR, the impedance of which changes on flexure or bending of the flexible sensor 2302. The flexible carrier layer 2304 is able to flex thus enabling the sensor 2302 to conform to the curvature of a surface of a subject to which the sensor 2302 is applied.

The flexible carrier layer 2304 is preferably made from a material that, whilst being flexible, is not able to stretch substantially in a direction perpendicular to the surface of a subject to which the layer 2304 may conform. As such, flexing of the carrier layer 2304 and, therefore, the flexible sensor 2302 leads to a change in resistance of the flexible sensor 2302 (when an FSR) or otherwise leads to a change in characteristics of the flexible sensor 2302. The sensor assembly 2300 further comprises a fixation device 2306 for maintaining the sensor assembly 2300 in position relative to a subject. For example, the fixation device 2306 is an anchoring point for attaching the sensor assembly 2300 to a carrier, such as a garment worn by a subject. The garment may be a shirt, strap, belt, vest, or the like. Equally, the sensor assembly 2300 is able to be worn in the pocket of a garment in the absence of the fixation device 2306. Any of the conditioning or signal processing modules or circuitry described above in relation to the sensor assemblies 100, 200 is equally able to be used to condition or generate signals from the flexible sensor 2302.

In use, the sensor assembly 2300 is positioned at a fixed location on a surface of a subject 2500 having a varying radius of curvature over time. For example, as shown in FIG. 28, the sensor assembly 2300 is fixed to the thorax of a subject 2500. Expansion of the thorax during breathing causes the flexible sensor 2302 to flex thus changing the characteristics (resistance or otherwise) of the flexible sensor 2302.

FIG. 29 graphically illustrates a clear periodic breathing signal generated from the flexible sensor 2302 of the sensor assembly 2300 integrated into the seam of a shirt worn the subject 2500 as shown in FIG. 28.

FIG. 30 shows a schematic, cross-sectional view of a sensor assembly 2700 which is a variation of the sensor assembly 2300, where, with reference to FIGS. 26 and 27, like reference numerals refer to like parts unless otherwise specified. The sensor assembly 2700 further comprises a flexible displacement sensor 2702 configured to generate a velocity signal representing a speed or velocity of displacement of the sensor 2702. The displacement sensor 2702 is coupled to a rear surface of the flexible carrier layer 2304. The displacement sensor 2702 is, optionally, at least partially encapsulated in an additional flexible carrier layer 2704. In an embodiment, the displacement sensor 2702 is a piezoelectric sensor.

FIG. 31 shows a schematic, cross-sectional view of a sensor assembly 2800 which is a variation of the sensor assembly 2700, where, with reference to FIG. 30, like reference numerals refer to like parts unless otherwise specified. The sensor assembly 2800 additionally comprises a second force sensor 2802, similar to the force sensor 202 of the assembly 200 shown in FIG. 1b, mounted to the displacement sensor 2702. The second force sensor 2802 is, optionally, at least partially encapsulated in a flexible carrier layer 2704 similar to the flexible carrier layer 2304 of the sensor assembly 2700. Like the force sensor 202, the force sensor 2802 changes in resistance upon external pressure applied to the assembly 2800. Thus, such externally applied force (and associated artefacts) can be accounted for and the flexible sensor 2302 calibrated accordingly.

Operation of the sensor assemblies 2700, 2800 is similar to that of respective sensor assemblies 100, 200 and so will not be described in detail again here.

FIGS. 32 and 33 illustrate that the sensor assemblies 100, 200 can be used for measuring pulse transit time (PTT) and variations in PTT with increase in the subject's blood pressure.

Sensor assemblies 100, 200 were placed on a healthy subject's chest wall and on the right common iliac artery of the subject. Trace 3202 represents the velocity of a pulse detected by the displacement sensor 104, after removal of respiration artefacts, at the iliac crest and trace 3204 represents the velocity of the pulse detected by the displacement sensor 104, after removal of respiration artefacts at the chest wall of the subject, in proximity to the apex of the subject's heart.

In FIG. 32, the traces 3202 and 3204 are measured prior to the subject undertaking exercise, more particularly, push-ups. It is noted that, prior to the subject undertaking the exercise, the iliac-apex lag was approximately 146 ms based on the healthy subject's resting blood pressure of 123/68. FIG. 33 shows that the PTT lag decreases substantially after exercise and an increase in the blood pressure of the subject to 144/79. After exercise, the iliac-apex lag reduces to approximately 59 ms. This demonstrates that the sensor assemblies 100, 200 are able to be used to detect PTT while the sensor assemblies 100, 200 are attached to a subject.

FIGS. 34-36 illustrate the use of the sensor assemblies 100, 200 for measuring cardiac activity, more particularly, cardiac stroke volume during exercise by a healthy subject. FIG. 34 shows various parameters with the healthy subject at rest. FIG. 35 shows those parameters with the subject undertaking weightlifting at a first, low rate and FIG. 36 shows the same parameters with the subject undertaking weightlifting at a second, higher rate.

In this test, a sensor assembly 100, 200 was attached to the chest wall of the subject. The subject was then required to lift a weight at two different rates to achieve two different effort levels. In these figures, trace 3402 represents the low-frequency force cardiogram (FCG) as measured by the force sensor 102 of the sensor assembly 100, 200. Trace 3404 represents the high frequency FCG as measured by the force sensor 102 of the sensor assembly 100, 200. Trace 3406 represents respiratory effort as measured by the displacement sensor 104 of the sensor assembly 100, 200. Trace 3408 represents a standard ECG and is provided for comparative purposes.

The results clearly demonstrate a consistent increase in amplitude in both the low-frequency and a high-frequency FCGs which is proportional to the effort level of the subject's heart. In particular, with respect to the values of the FCGs measured prior to exercise, the amplitude of the low-frequency FCG doubled in response to weight lifting at the low rate and trebled in response to the weightlifting at the higher rate. Conversely, the high-frequency FCG, which is known to be highly correlated with a seismocardiogram as extracted by the displacement sensor 104, increased by approximately 1.5 times in response to weightlifting at the low rate and almost double in response to weightlifting at the higher rate. These results demonstrate that the two FCG components carry different information on cardiac mechanics with the low-frequency FCG being more correlated with stroke volume than the high-frequency FCG.

One or more of the sensor assemblies described herein may be integrated in any combination into a medical device for in situ monitoring of a subject in various situations. For example, the sensor assemblies are able to be mounted in or on a mattress, a seat or a chair configured to monitor one of more physiological parameters of the subject (such as any of those described above). In addition the sensor assemblies may be configured to detect and monitor movement and position of the subject relative to the sensor assemblies on a bed or mattress. Such monitoring may be advantageous in the prevention of bed sores (where the sensor assembly/assemblies is/are integrated into a mattress or the like.

It will be appreciated that embodiments of the present disclosure may be used in the diagnosis and monitoring of a multitude of human and animal diseases and conditions where such diseases and conditions can be diagnosed and monitored by measurements of force, displacement, and/or acceleration of the skin. Non-limiting examples of cardiac conditions and diseases include innocent murmur, sclerosis, hypertension, angina pectoris, myocardial infarction, ventricular aneurysm, mitral valve prolapse (MVP), isolated click and murmur, mitral regurgitation, mitral stenosis (MS), tricuspid regurgitation (TR), mitral regurgitation, aortic regurgitation, aortic stenosis, hypertrophic obstructive cardiomyopathy, cardiomyopathy, pericarditis, pulmonary hypertension, atrial septal defect, ventricular septal defect, patent ductus arteriosus, pulmonary stenosis, coarctation of the aorta, tetralogy of fallot, coronary disease, heart failure, systolic heart failure, diastolic heart failure, pulmonary embolism, cor pulmonale, or the like.

Pulmonary diseases and conditions of the lungs may also be diagnosed, including lung congestion. Embodiments of the present disclosure may also be used to diagnose and monitor sleep disorders such as sleep apnoea, for example by placing one or more sensor assemblies as described herein at or near the trachea or at other positions around the neck of a subject. The sensor assemblies may be configured to monitor snoring, swallowing, muscle contraction around an airway (e.g. trachea), size reduction in the airway, optionally in addition to respiration.

Arterial and/or venous conditions (calcification, collapse etc.) may be diagnosed and monitored by placing one or more sensor assemblies described herein on the skin at or near an artery to be monitored. In some embodiments, for example, sensor assemblies may be positioned bilaterally at respective left and right arteries and a comparison may be made between left and right arteries to determine a condition of one or the other of the arteries (or both).

In any of the embodiments described above, sensor assemblies may be integrated into wearable devices for short or long term use and force, velocity and/or acceleration measurements may be collected and stored so that conditions and disease can be monitored over time.

Sensor assemblies described herein may also be used to monitor uterine contractions during pregnancy. A pregnant subject may wear one or more sensor assemblies at location(s) on the skin proximate the uterus, the contraction causing force displacement of the skin and corresponding signals being derived from the force and displacement sensors and optional accelerometers of the sensor assemblies.

Sensor assemblies described herein may not only be used to measure, diagnose, and monitor human or animal subjects, but may also be used to monitor foetal activity in such subjects. For example, one or more sensor assemblies, such as sensor assemblies 100, 200, may be placed at locations about the stomach to monitor movement, respiration, and cardiac signals of a foetus in the womb of an animal or human subject in a manner similar to that described above with reference to the human or animal subject itself.

In embodiments described herein, particularly with reference to FIGS. 3 to 5, sensor assemblies are fixed to the front of the torso. For example, FIG. 4 shows sensor assemblies being positioned at frontal auscultation positions. It will be appreciated that one or more sensor assemblies may be fixed to the back of the torso of an animal or human subject, for example at standard auscultation positions on the back of the torso without departing from the scope of the present disclosure.

It should be understood, especially by those having ordinary skill in the art with the benefit of this disclosure, that the various operations described herein, particularly in connection with the figures, may be implemented by other circuitry or other hardware components. The order in which each operation of a given method is performed may be changed, and various elements of the systems illustrated herein may be added, reordered, combined, omitted, modified, etc. It is intended that this disclosure embrace all such modifications and changes and, accordingly, the above description should be regarded in an illustrative rather than a restrictive sense.

Similarly, although this disclosure makes reference to specific embodiments, certain modifications and changes can be made to those embodiments without departing from the scope and coverage of this disclosure. Moreover, any benefits, advantages, or solutions to problems that are described herein with regard to specific embodiments are not intended to be construed as a critical, required, or essential feature or element.

Further embodiments likewise, with the benefit of this disclosure, will be apparent to those having ordinary skill in the art, and such embodiments should be deemed as being encompassed herein.

For many applications embodiments may be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog™ or VHDL (Very high speed integrated circuit Hardware Description Language). As the skilled person will appreciate, the code may be distributed between a plurality of coupled components in communication with one another. Where appropriate, the embodiments may also be implemented using code running on a field-(re) programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general purpose processor or the like. A module may itself comprise other modules or functional units. A module may be provided by multiple components or sub-modules which need not be co-located and could be provided on different integrated circuits and/or running on different processors.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An apparatus for sensing a physiological parameter of a subject, the apparatus comprising:
   a force sensor having a bandpass filter with a passband range between 20 Hz and 300 Hz, wherein the force sensor is configured to generate a filtered signal representing force displacement of an organ of the subject;
   a displacement sensor associated with the force sensor, the displacement sensor configured to generate a second signal representing displacement velocity of the organ of the subject; and
   a coupler arranged on one of the force sensor and the displacement sensor, the coupler configured to mechanically couple the force sensor and the displacement sensor with the organ; and
   wherein the coupler has a maximum planar surface area which is less than or equal to a maximum planar surface area of the force sensor.

2. The apparatus of claim 1, wherein the force sensor comprises a first force-sensing resistor (FSR).

3. The apparatus of claim 1, wherein the displacement sensor comprises a piezoelectric sensor.

4. The apparatus of claim 1, wherein the maximum planar surface area of the coupler approximates a maximum planar surface area of the displacement sensor.

5. The apparatus of claim 1, wherein the force sensor is mounted to the displacement sensor.

6. The apparatus of claim 5, wherein the force sensor comprises an operatively front surface coupled to an operatively, rear surface of the coupler and an operatively rear surface coupled to an operatively front surface of the displacement sensor.

7. The apparatus of claim 1, wherein the force sensor and the displacement sensor each have an operatively front surface coupled to an operatively rear surface of the coupler.

8. The apparatus of claim 7, wherein the force sensor and the displacement sensor are arranged concentrically on the operatively rear surface of the coupler.

9. The apparatus of claim 8, wherein the coupler comprises an operatively front surface configured to contact the organ and wherein the operatively front surface is one of dome shaped, mushroom shaped, cone shaped, and pyramid shaped.

10. The apparatus of claim 1, wherein the coupler is cylindrical or cuboid.

11. The apparatus of claim 1, wherein the coupler comprises at least one of a rigid plastics material and a conductive material.

12. The apparatus of claim 11, wherein the rigid plastics material comprises acrylic resin.

13. The apparatus of claim 12, wherein the second force sensor is a force-sensing resistor (FSR).

14. The apparatus of claim 13, wherein the second force sensor is coupled to an operatively rear surface of the displacement sensor.

15. The apparatus of claim 1, further comprising a second force sensor configured to measure a force applied to an operatively rear surface of the apparatus.

16. The apparatus of claim 15, wherein the second force sensor is coupled to an operatively rear surface of the displacement sensor.

17. The apparatus of claim 15, further comprising a fixing device configured to secure the apparatus to the organ of the subject.

18. The apparatus of claim 17, wherein the fixing device comprises at least one of:
   a) a strap;
   b) a belt;
   c) an adhesive patch.

19. The apparatus of claim 17, further comprising at least one processor configured to determine the physiological parameter based on the first signal and the second signal.

20. The apparatus of claim 19, wherein the at least one processor is configured to calibrate the second signal received from the displacement sensor based on the first signal.

21. The apparatus of claim 19, wherein the at least one processor is configured to calibrate the first signal and the second signal based on a third signal received from a second force sensor.

22. The apparatus of claim 19, wherein the physiological parameter comprises at least one of cardiac impulse, blood pressure, uterine contraction, fetal activity, respiration, an opening time of a heart valve of the subject, a closure time of a heart valve of the subject, a contractility level of a heart of the subject, a stroke volume of the heart of the subject, a cardiac output, and a blood pulse transit time.

23. The apparatus of claim 22, wherein the physiological parameter is blood pressure and the parameter to be measured comprises at least one of central blood pressure and peripheral blood pressure.

24. An apparatus for sensing a physiological parameter of a subject, the apparatus comprising:
   a force sensor having a bandpass filter with a passband range between 8 Hz and 40 Hz, wherein the force sensor is configured to generate a filtered signal representing force displacement of an organ of the subject;
   a displacement sensor associated with the force sensor, the displacement sensor configured to generate a second signal representing displacement velocity of the organ of the subject; and
   a coupler arranged on one of the force sensor and the displacement sensor, the coupler configured to mechanically couple the force sensor and the displacement sensor with the organ; and
   wherein the coupler has a maximum planar surface area which is less than or equal to a maximum planar surface area of the force sensor.

25. An apparatus for sensing a physiological parameter of a subject, the apparatus comprising:
   a force sensor having a bandpass filter with a passband range between 0.5 Hz and 8 Hz, wherein the force sensor is configured to generate a filtered signal representing force displacement of an organ of the subject;
   a displacement sensor associated with the force sensor, the displacement sensor configured to generate a second signal representing displacement velocity of the organ of the subject; and
   a coupler arranged on one of the force sensor and the displacement sensor, the coupler configured to mechanically couple the force sensor and the displacement sensor with the organ; and
   wherein the coupler has a maximum planar surface area which is less than or equal to a maximum planar surface area of the force sensor.

26. An apparatus for sensing a physiological parameter of a subject, the apparatus comprising:
   a force sensor having a bandpass filter with a low pass threshold of about 0.5 Hz, wherein the force sensor is configured to generate a filtered signal representing force displacement of an organ of the subject;
   a displacement sensor associated with the force sensor, the displacement sensor configured to generate a second signal representing displacement velocity of the organ of the subject; and
   a coupler arranged on one of the force sensor and the displacement sensor, the coupler configured to mechanically couple the force sensor and the displacement sensor with the organ; and
   wherein the coupler has a maximum planar surface area which is less than or equal to a maximum planar surface area of the force sensor.

* * * * *